(12) United States Patent
Scheidt et al.

(10) Patent No.: US 7,851,640 B2
(45) Date of Patent: Dec. 14, 2010

(54) CATALYTIC ENANTIOSELECTIVE SYNTHESIS OF FLAVANONES AND CHROMANONES

(75) Inventors: Karl Scheidt, Evanston, IL (US); Margaret Marie Biddle, Evanston, IL (US)

(73) Assignee: Northwestern University, Evanston, IL (US)

( * ) Notice: Subject to any disclaimer, the term of this patent is extended or adjusted under 35 U.S.C. 154(b) by 43 days.

(21) Appl. No.: 12/380,688

(22) Filed: Mar. 2, 2009

(65) Prior Publication Data
US 2009/0259055 A1    Oct. 15, 2009

Related U.S. Application Data

(60) Provisional application No. 61/032,541, filed on Feb. 29, 2008.

(51) Int. Cl.
C07D 311/32    (2006.01)
C07D 311/22    (2006.01)
C07D 311/92    (2006.01)

(52) U.S. Cl. .................... 549/403; 549/402; 549/401; 549/389

(58) Field of Classification Search ............. 549/403, 549/402, 401, 389
See application file for complete search history.

(56) References Cited

PUBLICATIONS

Chem. Abstracts, 21:10384 (1926), Abstract of Simonis, Berichte, vol. 59 B, p. 2908-2913 (1926).*
Chem. Abstracts, 58:59697 (1961), Abstract of French Patent 1,215,226 (1961).*
Moriarity et al, European J. of Medicinal Chem., vol. 41, p. 263-267 (2006).*
Takemoto, Y. "Recognition and activation by ureas and thioureas: stereoselective reactions using ureas and thioureas as hydrogen-bonding donors." Org. Biomol. Chem., 2005, 3, pp. 4299-4306.
Vakulya, B.; Varga, S.; Csámpai, A.; Soós, T. "Highly Enantioselective Conjugate Addition of Nitromethane to Chalcones Using Bifunctional Cinchona Organocatalysts." Organic Letters, 2005, vol. 7, No. 10, pp. 1967-1969.
Kanemitsu, T.; Yamashita, Y; Nagata, K.; Itoh, T. "Catalytic Asymmetric Synthesis of (R)-(—)-Calycotomine, (S)-(—)-Salsolidine and (S)-(—)-Carnegine." Synlett, 2006, No. 10, pp. 1595-1597.
Gaffield, W. "Circular Dichroism, Optical Rotatory Dispersion and Absolute Configuration of Flavanones 3-Hydroxyflavanones and their Glycosides. Determination of Aglycone Chirality in Flavanone Glycosides." Tetrahedron, vol. 26, pp. 4093-4108. Pergamon Press 1970. Presented in part at the 154th National Meeting of the American Chemical Society, Abstracts, p. S-113, Chicago, IL, Sep. 10-15, 1967.
Bernardi, L.; Fini, F.; Herrara, R.P.; Ricci, A.; Sgarzani, V. "Enantioselective aza-Henry reaction using cinchona organocatalysts." Tetrahedron 62 (2006), pp. 375-380.

Okino, T.; Hoashi, Y.; Takemoto, Y. "Thiourea-catalyzed nucleophilic additional of TMSCN and ketene silyl acetals to nitrones and aldehydes." Tetrahedron Letters 44 (2003) pp. 2817-2821.
Hoashi, Y.; Yabuta, T.; Takemoto, Y. "Bifunctional thiourea-catalyzed enantioselective double Michael reaction of γ,δ-unsaturated β-ketoester to nitroalkene: asymmetric synthesis of (—)-epibatidine." Tetrahedron Letters 45 (2004) pp. 9185-9188.
Li, H.; Wang, J.; Zu, L.; Wang, W. "Organocatalytic asymmetric conjugate addition of thioacetic acid to β-nitrostyrenes." Tetrahedron Letters 47 (2006) pp. 2585-2589.
Li, H; Zu, L.; Wang, J.; Wang, W. "Organocatalytic enantioselective Michael addition of thioacetic acid to enones." Tetrahedron Letters 47 (2006) pp. 3145-3148.
Morokuma, K.; Taira, Y; Uehara, Y.; Shibahara, S.; Takahashi, K.; Ishihara, J.; Hatakeyama, S. "Asymmetric Synthesis of (+)-trachyspic acid." Tetrahedron Letters 49 (2008) pp. 6043-6045.
Yoon, T.P.; Jacobsen, E.N. "Highly Enantioselective Thiourea-Catalyzed Nitro-Mannich Reactions." Angew. Chem. Int. Ed. 2005, 44, pp. 466-468.
Berkessel, A.; Cleemann, F.; Mukherjee, S.; Müller, T.N.; Lex, J. "Highly Efficient Dynamic Kinetic Resolution of Azlactones by Urea-Based Bifunctional Organocatalysts." Angew. Chem. Int. Ed. 2005, 44, pp. 807-811.
Hoashi, Y.; Okino, T.; Takemoto, Y. "Enantioselective Michael Addition to α,γ-Unsaturated Imides Catalyzed by a Bifunctional Organocatalyst." Angew. Chem. Int. Ed. 2005, 44, pp. 4032-4035.
McCooey S.H.; Connon, S.J. "Urea- and Thiourea-Substituted Cinchona Alkaloid Derivatives as Highly Efficient Bifunctional Organocatalysts for the Aysmmetric Addition of Malonate to Nitroalkenes: Inversion of Configuration at C9 Dramatically Improves Catalyst Performance." Angew. Chem. Int. Ed. 2005, 44, pp. 6367-6370.
Berkessel, A.; Cleeman, F.; Mukherjee, S. "Kinetic Resolution of Oxazinones: An Organocatalytic Approach to Enantiomerically Pure β-Amino Acids." Angew. Chem. Int. Ed. 2005, 44, pp. 7466-7469.
Marcelli, T.; Van Der Haas, R.N.S.; Van Maarseveen, J.H.; Hiemstra, H. "Asymmetric Organocatalytic Henry Reaction." Angew. Chem. Int. Ed. 2006, 45, pp. 929-931.
Taylor, M.S.; Jacobsen, E.N. "Asymmetric Catalysis by Chiral Hydrogen-Bond Donors." Angew. Chem. Int. Ed. 2006, 45, pp. 1520-1543.
Ye, J.; Dixon, D.J.; Hynes, P.S. "Enantioselective organocatalytic Michael addition of malonate esters to nitro olefins using bifunctional cinchonine derivatives." Chem. Commun., 2005, pp. 4481-4483.
Tillman, A.L.; Ye, J.; Dixon, D.J. "Direct enantio- and diastereoselective Mannich reactions of malonate and β-keto esters with N-Boc and N-Cbz aldimines catalysed by an bifunctional cinchonine derivative." Chem. Commun., 2006, pp. 1191-1193.
Connon, S.J. "Organocatalysis Mediated by (Thio)urea Derivatives." Chem. Eur. J. 2006. 12, pp. 5418-5427.

(Continued)

*Primary Examiner*—Bernard Dentz
(74) *Attorney, Agent, or Firm*—Reinhart Boerner Van Deuren s.c.

(57) ABSTRACT

Various chromanone, flavanone and abyssinone compounds as can be prepared enantioselectively using a chiral thiourea catalyst.

17 Claims, 2 Drawing Sheets

OTHER PUBLICATIONS

Tsogoeva, S.B.; Yalalov, D.A.; Hateley, M.J.; Weckbecker, C.; Huthmacher, K. "Asymmetric Organocatalysis with Novel Chiral Thiourea Derivatives: Bifunctional Catalysts for Strecker and Nitro-Michael Reactions." Eur. J. Org. Chem. 2005, 4995-5000.

Okino, T.; Hoashi, Y.; Takemoto, Y. "Enantioselective Michael Reaction of Malonates to Nitroolefins Catalyzed by Bifunctional Organocatalysts." J. Am. Chem. Soc. 2003, 125, pp. 12672-12673.

Taylor, M.S.; Jacobsen, E.N. "Highly Enantioselective Catalytic Acyl-Pictet—Spenger Reactions." J. Am. Chem. Soc. 2004, 126, pp. 10558-10559.

Okino, T.; Hoashi, Y.; Furukawa, T.; XU, X.; Takemoto, Y. "Enantio- and Diastereoselective Michael Reaction of 1,3-Dicarbonyl Compounds to Nitroolefins Catalyzed by a Biofunctional Thiourea." J. Am. Soc., 2005, 127, pp. 119-125.

Fuerst, D.E.; Jacobsen, E.N. "Thiourea-Catalyzed Enantioselective Cyanosilylation of Ketones." J. Am. Chem. Soc. 2005, 127, pp. 8964-8965.

Mattson, A.E.; Zhuk; A.M.; Reynolds, T.E.; Scheidt, K.A. "Direct Nucleophilic Acylation of Nitroalkenes Promoted by a Flouride Anion/Thiourea Combination." J. Am. Chem. Soc., 2006, 128, pp. 4932-4933.

Song, J.; Wang, Y.; Deng, L. "The Mannich Reaction of Malonated with Simple Imines Catalyzed by Bifunctional Cinchona Alkaloids: Enantioselective Synthesis of β-Amino Acids." J. Am. Chem. Soc. 2006, 128, pp. 6048-6049.

Wang, J.; LI, H.; Zu, L.; Jiang, W.; Xie, H.; Duan, W.; Wang, W. "Organocatalytic Enantioselective Conjugate Additions to Enones." J. Am. Chem. Soc. 2006, 128, pp. 12652-12653.

Kyle, E.; Neckers, L.; Takimoto, C; Curt, G; Bergan, R. "Genistein-induced apoptosis of prostate cancer cells is preceded by a specific decrease in focal adhesion kinase activity." Molecular Pharmacology (1997), 51(2), 192-200. abstract.

* cited by examiner

CATALYTIC ENANTIOSELECTIVE SYNTHESIS OF FLAVANONES AND CHROMANONES

This application claims priority benefit of application Ser. No. 61/032,541 filed Feb. 29, 2008, the entirety of which is incorporated herein by reference.

This invention was made with government support under Grant No. AG000260 awarded by the National Institutes of Health. The government has certain rights in the invention.

BACKGROUND OF THE INVENTION

The flavanone structure is abundant in natural products that possess a broad array of biological activity. Due to their favorable anti-tumor and anti-inflammatory properties, flavanones have been investigated as selective estrogen receptor modulators and TNF-α inhibitors. A limited number of strategies have been developed for the asymmetric synthesis of flavanones, such as resolution of the related alcohols or substitution reactions. Recently, an asymmetric copper(I)-catalyzed diethylzinc addition to 2-chromene was reported with high enantioselectivity. In this approach, the addition of benzaldehyde is required to trap the resulting zinc enolate. Ideally, asymmetric catalysis could provide a direct route to natural and synthetic flavanones that are currently difficult to access in optically active form. An enantioselective synthesis of flavanones that controls the C2 stereocenter remains a significant challenge due to the potential for reversible phenoxide elimination to form the achiral 2'-hydroxy chalcones. Accordingly, a route to enantioselective synthesis of flavanone and chromanone compounds remains an on-going concern in the art.

A related concern involves the abyssinones, a family of chiral, optically active flavanone natural products that display a diverse range of biological activities, including aromatase inhibition as well as antimicrobial, antimalarial activity. Despite their therapeutic promise, enantioenriched abyssinones have not been evaluated for their ability to inhibit cancer cell growth. This deficit is in large part due to the lack of efficient and stereoselective approaches for the synthesis of flavanones.

A limited number of strategies for the stereoselective synthesis of flavanones have been developed, including Mitsunobu reactions of chiral alcohols and acylation reactions of chiral ethers. Asymmetric conjugate addition reactions which are successful for dihydroquinolones (the nitrogen analogs of flavanones) are problematic due to undesired elimination reactions. As discussed above, the general structure of these molecules belies the challenge in executing a strategy that installs and maintains the configuration at the C2 position. This stereocenter is sensitive since basic conditions promote reversible ring opening to achiral 2'-hydroxy chalcones. Flavanones containing alkoxy- or hydroxy-substituents in the C4' position are particularly susceptible to racemization due to stabilized benzylic cation formation.

Although extracts containing these compounds have been used as traditional remedies, any investigation of specific anti-cancer properties of the optically enriched abyssinones requires a general synthetic approach beyond natural product isolation. From this perspective, an enantioselective synthesis would lead to realization of the benefits and advantages afforded by such compounds.

SUMMARY OF INVENTION

In light of the foregoing, it is an object of the present invention to provide various enantiomeric flavanone and chromanone compounds, corresponding intermediates and/or methods for their synthesis, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It can be an object of this invention to provide an asymmetric and/or enantioselective synthetic route to a variety of flavanone and/or chromanone compounds.

It can be another object of this invention to provide a method of using a chiral catalyst compound to effectively and efficiently access a range of enantiomeric or diastereometric natural and non-natural products, to assess biological activity and corresponding structure-activity relationships.

It can be another object of this invention, alone or in conjunction with one or more of the preceding objectives, to provide an asymmetric synthesis of natural (S)-abyssinone compounds and corresponding (R)-enantiomers, such compounds as can be used to inhibit tumor cell growth and/or regulate related metastatic behavior.

Other objects, features, benefits and advantages of the present invention will be apparent from this summary and the following descriptions of certain embodiments, and will be readily apparent to those skilled in the art having knowledge of various chromanone/flavanone compounds, related stereochemistries and corresponding synthetic techniques. Such objects, features, benefits and advantages will be apparent from the above as taken into conjunction with the accompanying examples, data, figures and all reasonable inferences to be drawn therefrom, alone or with consideration of the references incorporated herein.

In part, the present invention can be directed to a non-natural compound of a formula

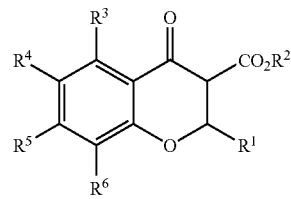

wherein $R^1$ can be selected from alkyl, cycloalkyl, cycloalkylalkyl, alkenyl, cycloalkylalkenyl, aryl, and aralkyl moieties, whether substituted or unsubstituted; $R^2$ can be selected from branched chain about $C_3$ to about $C_6$ alkyl and about $C_3$ to about $C_9$ cycloalkyl moieties, whether substituted or unsubstituted; $R^3$, $R^4$, $R^5$, and $R^6$ can be independently selected from H, $OR^7$, alkyl and cycloalkyl moieties, whether substituted or unsubstituted, and moieties where one of $R^6$ and $R^5$ together, $R^5$ and $R^4$ together, or $R^4$ and $R^3$ together form a $C_3$ to about $C_5$ alkylene or alkenylene moiety, whether substituted or unsubstituted; and $R^7$ can be selected from H and substituted or unsubstituted alkyl moieties.

In certain other embodiments, $R^3$-$R^7$ can be selected from various cycloalkylalkyl, alkenyl, cycloalkylalkyenyl, aryl and araalkyl moieties, whether such moieties are substituted or unsubstituted as discussed elsewhere herein. Regardless, such a compound can be present as an enol tautomer. Whether in the keto or enol form, such a compound can be present without limitation as to stereochemical configuration.

In certain such embodiments, $R^1$ can be selected from phenyl and substituted phenyl moieties. In certain such embodiments, the aforementioned substituents can be selected from hydroxy, alkyl, alkoxy, alkylene, halide moieties and combinations of such moieties. As illustrated below and discussed elsewhere herein, in certain non-limiting embodiments, $R^1$ can be selected from

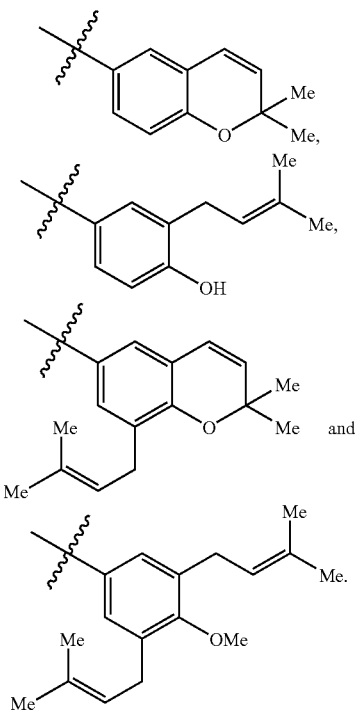

Regardless of $R^1$ identity, $R^2$ can be selected from tert-butyl and allyl moieties.

In part, the present invention can also be directed to a non-natural compound of a formula

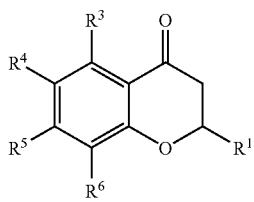

wherein $R^1$ can be selected from alkyl, cycloalkyl, cycloalkylalkyl, alkenyl, cycloalkylalkenyl, aryl, and aralkyl moieties, whether substituted or unsubstituted; $R^3$, $R^4$, $R^5$, and $R^6$ can be independently selected from H, $OR^7$, alkyl and cycloalkyl moieties, whether substituted a unsubstituted, and moieties where one of $R^6$ and $R^5$ together, $R^5$ and $R^4$ together, or $R^4$ and $R^3$ together form a $C_3$ to about $C_5$ alkylene or alkenylene moiety, whether substituted or unsubstituted; and $R^7$ can be selected from H and substituted or unsubstituted alkyl moieties.

In certain other embodiments, $R^3$-$R^7$ can be selected from various cycloalkylalkyl, alkenyl, cycloalkylalkyenyl, aryl and araalkyl moieties, whether such moieties are substituted or unsubstituted as discussed elsewhere herein. Regardless, such a compound can be present as an enol tautomer. Whether in the keto or enol form, such a compound can be present without limitation as to stereochemical configuration.

In certain embodiments, $R^1$ can be as discussed above and/or as comprising various phenyl and substituted phenyl moieties. In certain such embodiments, such a compound can be of a formula

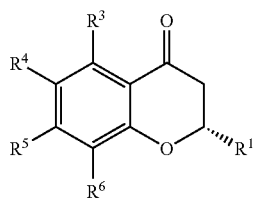

and comprising an (R)-stereochemical configuration at the C2 position thereof. In certain such embodiments, $R^1$ can be selected from

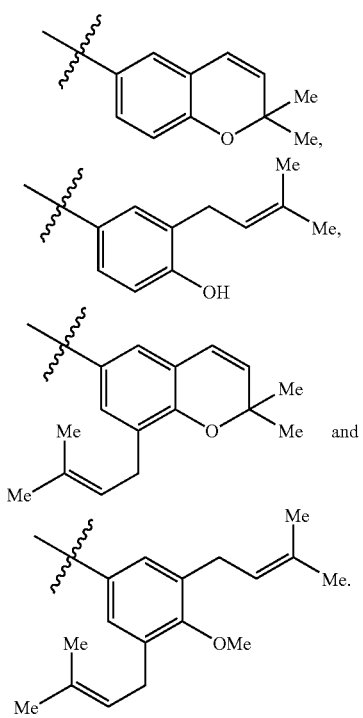

moieties.

In part, the present invention can also be directed to a method of using a chiral thiourea catalyst for enantioselective synthesis of a chromanone compound. Such a method can comprise providing an alkylidene compound of a formula

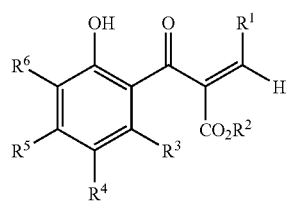

wherein $R^1$-$R^7$ can be as described above; and contacting such a compound with a chiral thiourea catalyst compound in an amount at least partially sufficient for intramolecular conjugate addition of such a alkylidene compound, to provide a chromanone compound of a formula

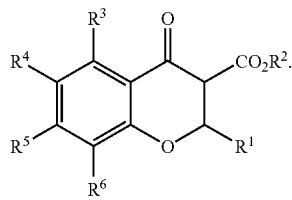

In certain non-limiting embodiments, such a method can comprise decarboxylation of such a chromanone compound. In certain such embodiments, $R^1$ can be aryl, and $R^5$ can be selected from H, alkyl, substituted alkyl, cycloalkyl and substituted cycloalkyl moieties. Regardless, a catalyst employed can be selected from catalyst compounds I, II and III, as illustrated below. In certain such embodiments, such a decarboxylated chromanone compound can have an (R) stereochemical configuration at the C2 position thereof. Optionally, where $R^1$ and $R^5$ are as discussed above, conjugate addition and decarboxylation can be achieved in a single reaction vessel, or without reaction vessel transfer. In such embodiments, a suitable catalyst can be compound III, as discussed below.

In certain other embodiments, optionally comprising decarboxylation, $R^1$ can be selected from

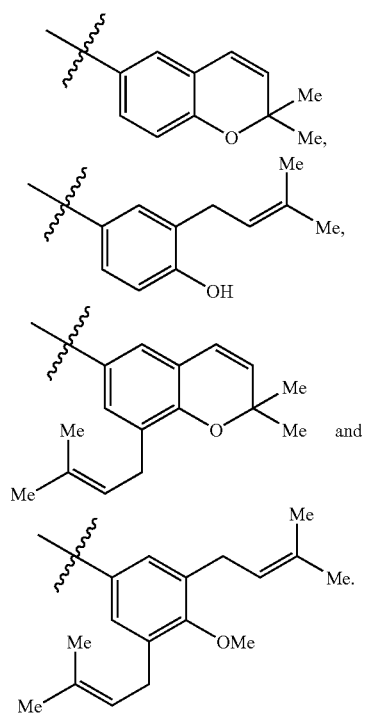

moieties and $R^5$ can be an allyl-protected hydroxy moiety. In certain such embodiments, a catalyst can be selected from compounds IV and V, as discussed below. Optionally, such a method can comprise decarboxylation and hydroxy deprotection in a single vessel, without reaction medium transfer. In certain such embodiments, catalyst compound IV can be utilized, and such a decarboxylated chromanone compound can have an (R) stereochemical configuration as the C2 position thereof. In certain other embodiments, catalyst compound V can be utilized, and such a decarboxylated chromanone compound can have an (S) stereochemical configuration at the C2 position thereof.

In part, the present invention can also be directed to a method of preparing a chromanone compound comprising an (R) stereochemical configuration at the C2 position thereof. Such a method can comprise providing a reaction medium comprising a mixture of a β-ketoester of a formula

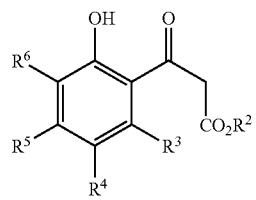

wherein $R^2$-$R^7$ can be as described above; an aldehyde of a formula $R^1$CHO, where $R^1$ can be selected from alkyl, cycloalkyl, cycloalkylalkyl, cycloalkylalkenyl, aryl and aralkyl moieties, whether substituted or unsubstituted; an organoamine base; and a thiourea catalyst selected from compounds I, II and III, to provide a C3-carboxy substituted chromanone compound; and contacting such a reaction medium with a $C_1$ to about $C_{10}$ organic acid, to decarboxylate such a chromanone compound. Such a method of preparation can be performed in a single reaction vessel, without transfer of the reaction medium from one vessel to another. In certain non-limiting embodiments, such a thiourea catalyst can be compound I, as discussed below. Regardless, in accordance with such a methodology, $R^1$ can be a phenyl-substituted ethyl moiety.

In part, the present invention can also be directed to one or more methods to affect metastatic pancreatic cancer cell growth and/or expression of a metastatic enzyme associated therewith. Such a method can comprise providing an abyssinone compound of the sort described herein; and contacting such a compound with a growth of pancreatic cancer cells. Such a compound can be selected from natural and non-natural abyssinone compounds and combinations thereof. In certain non-limiting embodiments, such an effect can be indicated by downregulation and/or reduced expression of matrix metalloproteinase type 2 enzyme by such cancer cells.

Such a method can be effected using an enantiomerically-enriched abyssinone compound, as can be provided through the synthetic techniques described herein. Without limitation, abyssinone compounds III and IV comprising an (R) stereochemical configuration at C2 can be used to downregulate expression of such a metastatic enzyme.

This invention can be considered in the context of new methods for catalytic and enantioselective synthesis. Without limitation, using chiral thiourea catalysts, aryl alkylidene β-ketoesters can be cyclized to the corresponding chromanones in good yields and high enantioselectivities. Alternatively, aryl β-ketoesters can be condensed with aldehydes and subsequently cyclized to the corresponding chromanone in a "one-pot" reaction. In either case, the 3-position ester of the chromanone may be removed without disturbing the optical integrity of the 2-position substituent. Thus, the present methods provide direct access to optically active natural and synthetic chromanones, including flavanones.

DETAILED DESCRIPTION OF CERTAIN EMBODIMENTS

Figure 1:
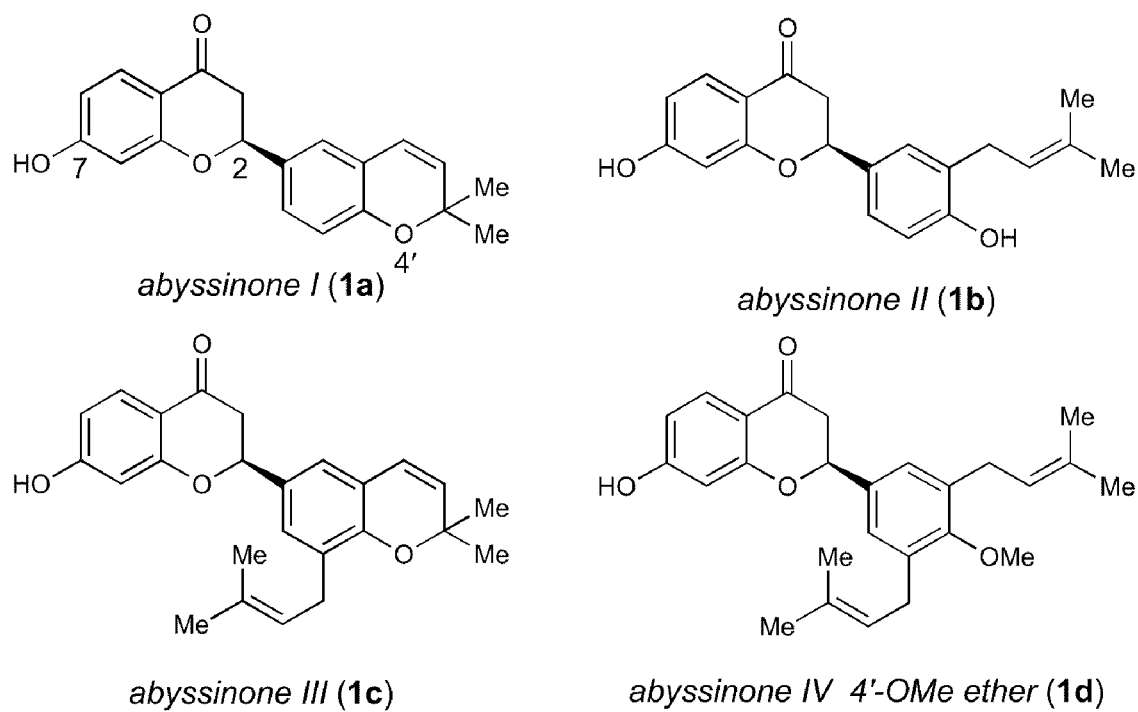
FIG. 1. Abyssinone Natural Products of the Prior Art.

In accordance with one aspect, the invention provides methods of preparing chromanones, including flavanones. The methods include contacting an alkylidene compound of a formula,

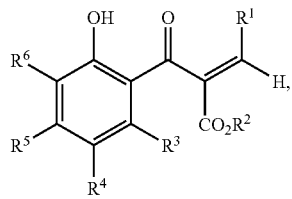

with an effective amount of chiral thiourea catalyst to produce a chromanone compound of a formula,

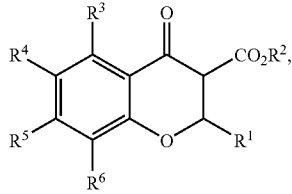

wherein
- $R^1$ is a substituted or unsubstituted alkyl, cycloalkyl, cycloalkylalkyl, alkenyl, cycloalkylalkenyl, aryl, or aralkyl group;
- $R^2$ is a substituted or unsubstituted branched chain $C_{3-6}$ alkyl or $C_{3-9}$ cycloalkyl group;
- $R^3$, $R^4$, $R^5$, and $R^6$ are independently selected from H, $OR^7$, or a substituted or unsubstituted alkyl or cycloalkyl group; and/or one of $R^6$ and $R^5$ together, $R^5$ and $R^4$ together, or $R^4$ and $R^3$ together may form a substituted or unsubstituted $C_{3-5}$ alkylene or alkenylene group; and
- $R^7$ is a substituted or unsubstituted alkyl group.

As indicated above, various alkylidene compounds may be used to produce a wide variety of chromanones. In some embodiments of the methods, $R^1$ is a substituted or unsubstituted alkyl, cycloalkyl, aryl, or aralkyl group. In other embodiments, $R^2$ is an unsubstituted branched chain $C_{3-4}$ alkyl group, such as, e.g., a t-butyl group. In some embodiments, $R^3$, $R^4$, $R^5$, and $R^6$ are independently selected from H, $OR^7$, or an unsubstituted $C_{1-6}$ alkyl group. In still other embodiments, $R^4$ and $R^5$ together form —$(CH_2)_4$— or —CH═CH—CH═CH—, providing chromanones having a tricyclic core.

Chiral thiourea catalysts employed in the present methods include a thiourea group, —NH—C(S)—NH—, a tertiary amine, and at least one chiral center. Chiral thiourea catalysts may have additional chiral centers such as 2, 3, or 4 chiral centers. Thus, cinchona and chiral cyclohexylamine thiourea catalysts are useful in the present methods. Exemplary chiral thiourea catalysts for use in the present methods include but are not limited to compounds of the sort shown below, or a mixture thereof:

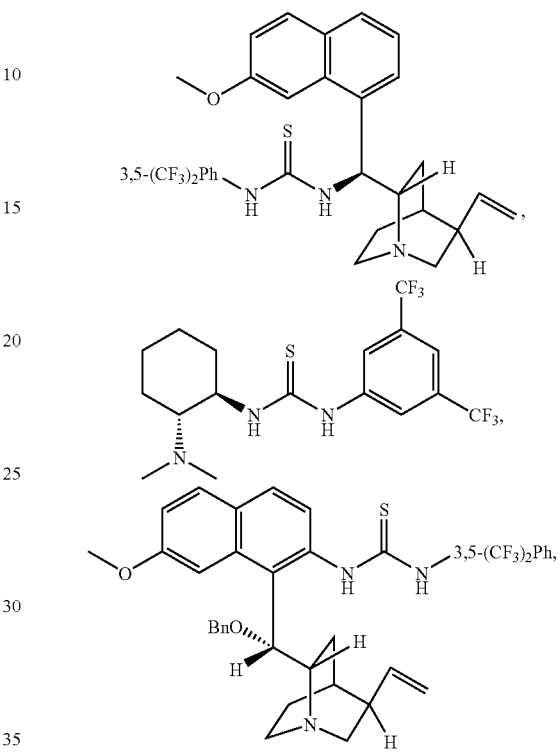

wherein 3,5-$(CF_3)_2$Ph is 3,5-ditrifluorophenyl and Bn is benzyl. Other chiral thiourea catalysts that may be used in the present methods including those described in Vakulya et al *Org. Lett.* 2005, 7, 1967-69; Mccooey et al. *Angew. Chem. Intl. Ed.* 2005, 44, 6367-6370; Ye et al. *Chem. Comm.* 2005, 4481-83; Bernardi et al. *Tetrahedron* 2006, 62, 375-80; Tillman, et al. *J. Chem. Comm.* 2006, 128, 4932-33; Song et al. *J. Am. Chem. Soc.* 2006, 128, 6048-49; Wang et al. *J. Am. Chem.* 2006, 128, 12652-53; Okino et al. *Tetrahedron Lett.* 2003, 44, 2817-21; Taylor et al. *J. Am. Chem. Soc.* 2004, 126, 10558-59; Berkessel et al. *Angew. Chem. Int. Ed.* 2005, 44, 807-11; Yoon et al. *Angew. Chem. Int. Ed.* 2005, 44, 466-68; Okino et al. *J. Am. Chem.* 2005, 127, 119-125; Fuerst et al. *J. Am. Chem.* 2005, 127, 8964-65; Hoashi et al. *Angew. Chem. Int. Ed.* 2005, 44, 4032-35; Tsogoeva et al. *Eur. J. Org. Chem.* 2005, 4995-5000; Berkessel et al. *Angew. Chem. Int. Ed.* 2005, 44, 7466-69; Li et al. *Tetrahedron Lett.* 2006, 47, 3145-48.

The chiral thiourea catalysts may be employed in the present methods in a wide range of amounts such as from about 1 mol percent to about 40 mol percent. In some embodiments, the chiral thiourea catalyst is used in an amount from about 5 mol percent to about 25 mol percent or from about 10 to about 20 mol percent. In view of the guidance provided herein, it is within the skill in the art to select an appropriate amount of chiral thiourea catalyst for the application at hand.

The present methods of producing a compound of Formula II may be conducted in any suitable organic solvent, such as, e.g., toluene, xylene, or benzene. The contacting step may also be carried out at a variety of temperatures ranging from about −50° C. to about 50° C., or from about −30 to ambient temperature (e.g., 15° C.-25° C.).

In some embodiments, the present methods provide optically active chromanones. For example, a chromanone compound of a formula,

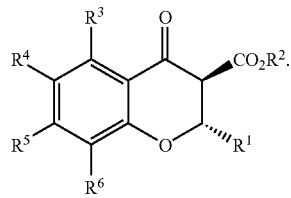

In some embodiments, the enantiomeric excess (ee) of such a compound is at least about 50%, at least about 60%, at least about 70%, at least about 80% or at least about 90%. In other embodiments, the ee ranges from about 70% to about 95%, to about 98%, to about 99% or to about 100%.

The ester group may be readily removed to provide the 2-substituted chromanone by, e.g., deprotection of the ester followed by decarboxylation. In some embodiments, $R^2$ is a t-butyl group. Thus, the present methods further include exposing a chromanone compound to an amount of acid sufficient to produce a decarboxylated compound of a formula,

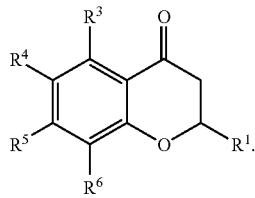

Any suitable acid may be used including, but not limited to toluenesulfonic acid or benzenesulfonic acid. Optionally the contacting step takes place at a temperature ranging from about 40° C. to about 140° C., more preferably from about 60° C. to about 100° C. In some embodiments of the present methods, such a compound has a structure of a formula,

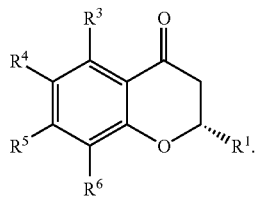

In another aspect of the present invention, a tandem Knoevenagel-cyclization reaction is provided. Thus, the present methods include contacting a β-ketoester compound of a formula,

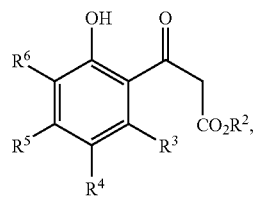

with aldehyde $R^1CHO$, an chiral thiourea catalyst, an organoamine base, a $C_{1-10}$ carboxylic acid, and optionally in the presence of molecular sieves (e.g., 4 Å sieves) to produce a compound of a formula,

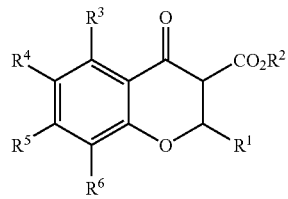

wherein
$R^1$ is a substituted or unsubstituted alkyl, cycloalkyl, cycloalkylalkyl, alkenyl, cycloalkylalkenyl, aryl, or aralkyl group;
$R^2$ is a substituted or unsubstituted branched chain $C_{3-6}$ alkyl or $C_{3-9}$ cycloalkyl group;
$R^3$, $R^4$, $R^5$, and $R^6$ are independently selected from H, $OR^7$, or a substituted or unsubstituted alkyl or cycloalkyl group; and/or one of $R^6$ and $R^5$ together, $R^5$ and $R^4$ together, or $R^4$ and $R^3$ together may form a substituted or unsubstituted $C_{3-5}$ alkylene group; and
$R^7$ is a substituted or unsubstituted alkyl group.

Typically, the contacting step and the compound production take place in the same reaction vessel. A variety of β-ketoester compounds and aldehydes may be used in the present methods. In addition to those listed above, in some embodiments, $R^1$ is a substituted or unsubstituted alkyl, cycloalkyl, aryl, or aralkyl group. In others, $R^2$ is an unsubstituted branched chain $C_{3-4}$ alkyl group, such as a t-butyl group. In still others, $R^3$, $R^4$, $R^5$, and $R^6$ are independently selected from H, $OR^7$, or an unsubstituted $C_{1-6}$ alkyl group. In some embodiments, $R^4$ and $R^5$ together form —$(CH_2)_4$— or —CH=CH—CH=CH—.

The same solvents, temperatures and chiral thiourea catalysts may be used in the tandem reaction as described herein. Suitable $C_{1-10}$ carboxylic acids include but are not limited to formic, acetic, propanoic, and benzoic acids. Suitable organoamine bases include secondary amines such as piperidine, diisopropylamine and the like. In some embodiments of the methods of producing chromanone compound is a compound of a formula,

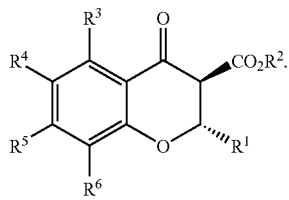

In some embodiments, the ee of such a compound is at least about 50%, at least about 60%, at least about 70%, at least about 80% or at least about 90%. In other embodiments, the ee ranges from about 70% to about 95%, 98% or 99%.

The present methods may further comprising exposing the chromanone compound from the tandem reaction to an amount of acid sufficient to produce a decarboxylated compound of a formula,

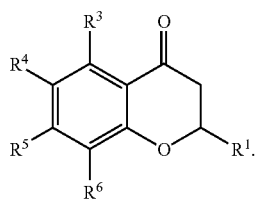

The following terms are used throughout as defined below.

In general, "substituted" refers to an organic group as defined below (e.g., an alkyl group) in which one or more bonds to a hydrogen atom contained therein are replaced by a bond to atoms other than hydrogen or unsubstituted carbon. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitriles (i.e. CN); and the like.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched alkyl groups having from 1 to 12 carbons or, in some embodiments, from 1 to 8, 1 to 6, or 1 to 4 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, isobutyl, sec-butyl, tert-butyl, neopentyl, isopentyl, and 2,2-dimethylpropyl groups. Representative substituted alkyl groups may be substituted one or more times with substituents such as those listed above.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 10 ring members, whereas in other embodiments the number of ring carbon atoms range from 3 to 5, 3 to 6, 3 to 7 or 3 to 8. Cycloalkyl groups further include mono-, bicyclic and polycyclic ring systems, such as, for example bridged cycloalkyl groups and fused rings, such as, but not limited to, decalinyl, and the like. Bridged cycloalkyl groups may be bicyclic, such as, for example, bicyclo[2.1.1]hexane, or tricyclic, such as, for example, adamantyl. In some embodiments, polycyclic cycloalkyl groups have three rings. Substituted cycloalkyl groups may be substituted one or more times with non-hydrogen and non-carbon groups as defined above. However, substituted cycloalkyl groups also include rings that are substituted with straight or branched chain alkyl, alkenyl or alkynyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 16 carbon atoms, and typically 4 to 10 carbon atoms. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain and cycloalkyl groups as defined above, except that at least one double bond exists between two carbon atoms. Thus, alkenyl groups have from 2 to 12 carbons or, in some embodiments, from 2 to 8, 2 to 6, or 2 to 4 carbon atoms. In some embodiments, alkenyl groups include cycloalkenyl groups having from 4 to 20 carbon atoms, 5 to 20 carbon atoms, 5 to 10 carbon atoms, or even 5, 6, 7 or 8 carbon atoms. Examples include, but are not limited to vinyl, allyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, cyclohexenyl, cyclopentenyl, cyclohexadienyl, butadienyl, pentadienyl, and hexadienyl, among others. Representative substituted alkenyl groups may be mono-substituted or substituted more than once, such as, but not limited to, mono-, di- or tri-substituted with substituents such as those listed above.

Cycloalkenylalkyl groups are alkyl groups as defined above in which a hydrogen or carbon bond of the alkyl group is replaced with a bond to a cycloalkenyl group as defined above. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Aryl groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6 to 10 carbon atoms in the ring portions of the groups. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 14 carbon atoms or, in some embodiments, 7 to 10 carbon atoms. Substituted aralkyl groups may be substituted at the alkyl, the aryl, or both the alkyl and the aryl portions of the group. Representative aralkyl groups include but are not limited to benzyl and phenethyl groups and fused (cycloalkylaryl)alkyl groups such as 4-ethyl-indanyl. Representative substituted aralkyl groups may be substituted one or more times with substituents such as those listed above.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

Alkyl, alkenyl, and alkynyl groups may be divalent as well as monovalent. The valency of an alkyl, alkenyl, or alkynyl group will be readily apparent from the context to those of skill in the art. For example, the alkyl group in an aralkyl group is divalent. In some embodiments, divalency is expressly indicated by appending the suffix "ene" or "ylene" to terms defined herein. Thus, for example, "alkylene" refers to divalent alkyl groups and alkenylene refers to divalent alkene groups.

The term "carboxylate" as used herein refers to a —COOH group.

The term "carboxylic ester" as used herein refers to —COOR$^{30}$ groups. R$^{30}$ is a substituted or unsubstituted alkyl, cycloalkyl, alkenyl, alkynyl, aryl, aralkyl, heterocyclylalkyl or heterocyclyl group as defined herein.

The term "amide" (or "amido") includes C- and N-amide groups, i.e., —C(O)NR$^{31}$R$^{32}$, and —NR$^{31}$C(O)R$^{32}$ groups, respectively. R$^{31}$ and R$^{32}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H).

Urethane groups include N- and O-urethane groups, i.e., —NR$^{33}$C(O)OR$^{34}$ and —OC(O)NR$^{33}$R$^{34}$ groups, respectively. R$^{33}$ and R$^{34}$ are independently hydrogen, or a substituted or unsubstituted alkyl, alkenyl, alkynyl, cycloalkyl, aryl, aralkyl, heterocyclylalkyl, or heterocyclyl group as defined herein.

The term "amine" (or "amino") as used herein refers to —NHR$^{35}$ and —NR$^{36}$R$^{37}$ groups, wherein R$^{35}$, R$^{36}$ and R$^{37}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is NH$_2$, methylamino, dimethylamino, ethylamino, diethylamino, propylamino, isopropylamino, phenylamino, or benzylamino.

The term "sulfonamido" includes S- and N-sulfonamide groups, i.e., —SO$_2$NR$^{38}$R$^{39}$ and —NR$^{38}$SO$_2$R$^{39}$ groups, respectively. R$^{38}$ and R$^{39}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—SO$_2$NH$_2$).

The term "thiol" refers to —SH groups, while sulfides include —SR$^{40}$ groups, sulfoxides include —S(O)R$^{41}$ groups, sulfones include —SO$_2$R$^{42}$ groups, and sulfonyls include —SO$_2$OR$^{43}$, R$^{40}$, R$^{41}$, R$^{42}$, and R$^{43}$ are each independently a substituted or unsubstituted alkyl, cycloalkyl, alkenyl, alkynyl, aryl aralkyl, heterocyclyl or heterocyclylalkyl group as defined herein.

The term "urea" refers to —NR$^{44}$—C(O)—NR$^{45}$R$^{46}$ groups. R$^{44}$, R$^{45}$, and R$^{46}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to —C(NR$^{47}$)NR$^{48}$R$^{49}$ and —NR$^{47}$C(NR$^{48}$)R$^{49}$, wherein R$^{47}$, R$^{48}$, and R$^{49}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to —NR$^{50}$C(NR$^{51}$)NR$^{52}$R$^{53}$ wherein R$^{50}$, R$^{51}$, R$^{52}$ and R$^{53}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to —C(R$^{54}$)=C(R$^{55}$)NR$^{56}$R$^{57}$ and —NR$^{54}$C(R$^{55}$)=C(R$^{56}$)R$^{57}$, wherein R$^{54}$, R$^{55}$, R$^{56}$ and R$^{57}$ are each independently hydrogen, a substituted or unsubstituted alkyl, cycloalkyl, alkenyl, alkynyl, aryl aralkyl, heterocyclyl or heterocyclylalkyl group as defined herein.

The term "imide" refers to —C(O)NR$^{58}$C(O)R$^{59}$, wherein R$^{58}$ and R$^{59}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to —CR$^{60}$(NR$^{61}$) and —N(CR$^{60}$R$^{61}$) groups, wherein R$^{60}$ and R$^{61}$ are each independently hydrogen or a substituted or unsubstituted alkyl, cycloalkyl, alkenyl, alkynyl, aryl aralkyl, heterocyclyl or heterocyclylalkyl group as defined herein, with the proviso that R$^{60}$ and R$^{61}$ are not both simultaneously hydrogen.

Those of skill in the art will appreciate that compounds of the invention may exhibit the phenomena of geometric isomerism and/or optical isomerism. As the formula drawings within the specification and claims can represent only one of the possible tautomeric, conformational isomeric, optical isomeric or geometric isomeric forms, it should be understood that the invention encompasses any optical isomeric and/or geometric isomeric forms of the compounds described herein, as well as mixtures of these various different forms.

Stereoisomers of compounds (also known as optical isomers) include all chiral, diastereomeric, and racemic forms of a structure, unless the specific stereochemistry is expressly indicated. Thus, compounds used in the present invention include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these are all within the scope of the invention.

More specifically, as relates to certain embodiments, the asymmetric synthesis of flavanones (3, R=aryl) and chromanones (3, R=alkyl) from α-substituted chalcones (1) proceeds by an intramolecular conjugate addition catalyzed by chiral thioureas (eq 1).

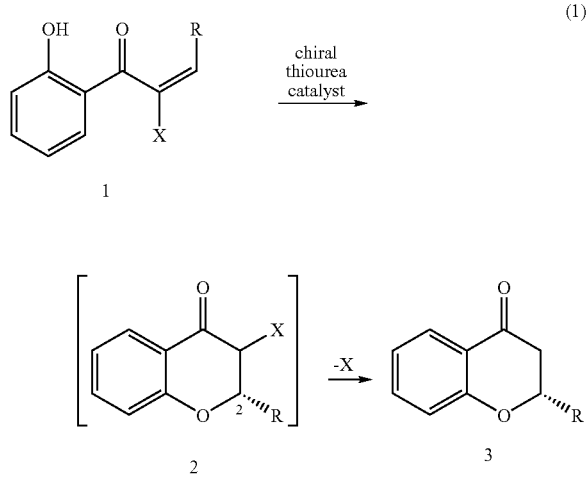

Intramolecular conjugate addition of a phenol to an activated unsaturated ketone is a way to access this oxygen heterocycle under mild conditions that minimizes elimination to the undesired chalcones. Such a strategy incorporates a functional group on the potential substrate that (a) enhances the reactivity of the conjugate acceptor, (b) favors the flavanone products over the acyclic chalcones and (c) provides a second Lewis basic site for potential interaction with a catalyst. (Scheme 1.) The tert-butyl ester group addresses these criteria and importantly, it is removable under mild conditions with minimal impact on the C2 stereochemistry.

the trans-2,3-diastereomer (entries 1-3). Surprisingly, lower reaction temperatures do not improve the level of enantioselectivity observed for catalysts I or II (Table 1, entries 4 and 5). Catalyst III is highly enantioselective (>90% ee) at lower temperatures and lower catalyst loadings (entry 6 vs. 7). Lowering the temperature beyond −25° C. does not improve selectivity and the unusual dependence of ee on loading has been observed in other thiourea-catalyzed reactions. Importantly, the parent 2'OH chalcone (4) does not undergo cyclization with I, II, or III, thus underscoring the importance of the carboxy group.

For developments and applications of cinchona-derived thioureas, see: (a) Vakulya, B.; Varga, S.; Csampai, A.; Soós, T. Org. Letters 2005, 7, 1967-1969. (b) Mccooey, S. H.; Connon, S. J. Angew. Chem., Int. Ed. 2005, 44, 6367-6370. (c) Ye, J. X.; Dixon, D. J.; Hynes, P. S. Chem. Commun. 2005, 4481-4483. (d) Bernardi, L.; Fini, F.; Herrera, R. P.; Ricci, A.; Sgarzani, V. Tetrahedron 2006, 62, 375-380. (e) Tillman, A. L.; Ye, J. X.; Dixon, D. J. Chem. Commun. 2006, 1191-1193. (f) Mattson, A. E.; Zuhl, A. M.; Reynolds, T. E.; Scheidt, K. A. J. Am. Chem. Soc. 2006, 128, 4932-4933. (g) Song, J.; Wang, Y.; Deng, L. J. Am. Chem. Soc. 2006, 128, 6048-6049. (h) Wang, J.; Li, H.; Zu, L. S.; Jiang, W.; Xie, H. X.; Duan, W. H.; Wang, W. J. Am. Chem. Soc. 2006, 128, 12652-12653, each of which is incorporated herein by reference.

For developments and applications of chiral cyclohexylamine-derived thiourea catalysis, see: (a) Okino, T.; Hoashi, Y.; Takemoto, Y. Tetrahedron Lett. 2003, 44, 2817-2821. (b) Taylor, M. S.; Jacobsen, E. N. J. Am. Chem. Soc. 2004, 126, 10558-10559. (c) Berkessel, A.; Cleemann, F.; Mukherjee, S.; Muller, T. N.; Lex, J. Angew. Chem., Int. Ed. 2005, 44, 807-811. (d) Yoon, T. P.; Jacobsen, E. N. Angew. Chem., Int.

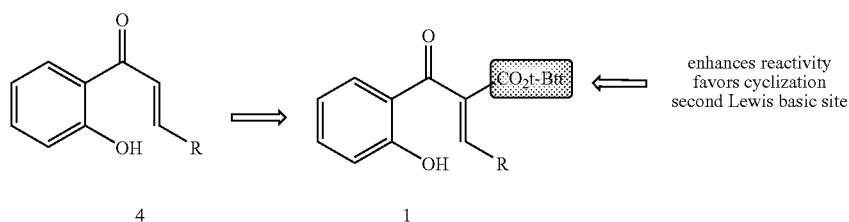

Scheme 1.

To test this hypothesis, the starting alkylidene β-keto esters 1 were accessed via Knoevenagel condensation. The E-alkene is isolated by crystallization in >95:5 E:Z for the aldehydes employed. A bifunctional catalyst activates the 1,3-dicarbonyl moiety of 1 and deprotonates the phenol, leading to the desired asymmetric conjugate addition. Accordingly, chiral thioureas containing a tertiary amine were surveyed as catalysts for the intramolecular conjugate addition (Table 1, eq 2). (For reviews of thiourea catalysis, see: (a) Takemoto, Y. Org. Biomol. Chem. 2005, 3, 4299-4306. (b) Taylor, M. S.; Jacobsen, E. N. Angew. Chem., Int. Ed. 2006, 45, 1520-1543. (c) Connon, S. J. Chem. Eur.-J. 2006, 12, 5418-5427, each of which is incorporated herein by reference.)

With reference to Table 1, below, thiourea catalysts I, II and III (at 20 mol % in toluene) provided good yields and encouraging selectivities for the 3-carboxy flavanone product 6 as Ed. 2005, 44, 466-468. (e) Okino, T.; Hoashi, Y.; Furukawa, T.; Xu, X. N.; Takemoto, Y. J. Am. Chem. Soc. 2005, 127, 119-125. (f) Fuerst, D. E.; Jacobsen, E. N. J. Am. Chem. Soc. 2005, 127, 8964-8965. (g) Hoashi, Y.; Okino, T.; Takemoto, Y. Angew. Chem., Int. Ed. 2005, 44, 4032-4035. (h) Tsogoeva, S. B.; Yalalov, D. A.; Hately, M. J.; Weckbecker, C.; Huthmacher, K. Eur. J. Org. Chem. 2005, 4995-5000. (i) Berkessel, A.; Cleemann, F.; Mukherjee, S. Angew. Chem., Int. Ed. 2005, 44, 7466-7469. (j) Li, H.; Zu, L. S.; Wang, J.; Wang, W. Tetrahedron Lett. 2006, 47, 3145-3148, each of which is incorporated herein by reference.

See also, generally Marcelli, T.; van der Haas, R. N. S.; van Maarseveen, J. H.; Hiemstra, H. Angew. Chem., Int. Ed. 2006, 45, 929-931. Li, H.; Wang, J.; Zu, L. S.; Wang, W. Tetrahedron Lett. 2006, 47, 2485-2589, each of which is incorporated herein by reference.

TABLE 1

Optimization of Enantioselective Conjugate Addition[a]

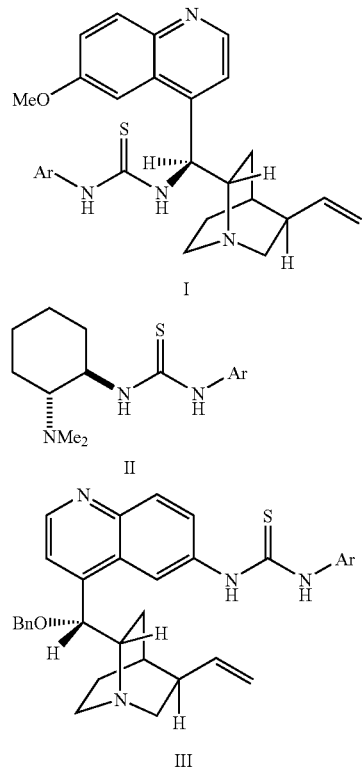

| entry | catalyst | mol % | temp (° C.) | ee (%)[b] | yield (%)[c] |
|---|---|---|---|---|---|
| 1 | I | 20 | 22 | −80 | 97 |
| 2 | II | 20 | 22 | 80 | 82 |
| 3 | III | 20 | 22 | 71 | 88 |
| 4 | I | 20 | −25 | −80 | 78 |
| 5 | II | 20 | −25 | 80 | nd[d] |
| 6 | III | 20 | −25 | 88 | nd[d] |
| 7 | III | 10 | −25 | 92 | 85 |

Ar = 3,5(CF$_3$)—Ph
[a]Reaction conditions: 0.1 M 5.
[b]Determined by HPLC analysis (Chiralcel OD-H).
[c]Yield after chromatography.
[d]Not determined.

An aspect of the process is that after cyclization, the 3-carboxy group can be removed by treatment with acid in toluene without compromising the integrity of the newly formed stereocenter at C2. For example, the exposure of 6 (89% ee) to p-TsOH in toluene at 70° C. affords the corresponding decarboxylated flavanone 7 in 88% ee. (The 4'-methoxyphenyl substrate (12, R=4-OMe-Ph) affords racemic product under p-TsOH conditions. The decarboxylation using MgBr$_2$.OEt$_2$ affords the 4'-methoxyflavanone in 78% ee.)

Because the thiourea-catalyzed conjugate addition and decarboxylation are performed in toluene, these reactions can be combined (i.e., one-pot or without reaction vessel transfer) into a single-flask synthesis of a variety of flavanones (Table 2). A variety of aryl groups can be accommodated on the starting alkenes and these compounds undergo cyclization with excellent enantioselectivity and good yields in the presence of 10 mol % III (entries 1-6). Many of the 3-carboxy flavanone products are formed as mixtures of cis and trans diastereomers, but the in situ decarboxylation delivers highly enantioenriched flavanones in excellent yield. Different phenol moieties can also be accommodated in the reaction including electron rich (entry 7) and extended aromatic substrates (entry 9). The cyclohexyl-substituted alkylidene also undergoes cyclization to afford chromanone 16 in good enantioselectivity (80% ee, entry 10).

TABLE 2

Scope of Cyclization/Decarboxylation[a]

| entry | R | R$^1$ | R$^2$ | product | ee (%)[b,c] | yield (%)[d] |
|---|---|---|---|---|---|---|
| 1 | Ph | H | H | 7 | 94 | 92 |
| 2 | 4-BrPh | H | H | 8 | 92 | 65 |
| 3 | 2-naphthyl | H | H | 9 | 91 | 89 |
| 4 | 4-CH$_3$—Ph | H | H | 10 | 90 | 83 |
| 5 | 2-Cl—Ph | H | H | 11 | 88 | 67 |
| 6 | 4-OMe—Ph | H | H | 12 | 91[e] | 94 |
| 7 | Ph | OMe | H | 13 | 89 | 71 |
| 8 | Ph | Me | H | 14 | 90 | 97 |
| 9 | Ph | —(CH)$_4$— | | 15 | 89 | 78 |
| 10 | cyclohexyl | H | H | 16 | 80 | 65 |

[a]Reaction conditions: 0.1 M of ester.
[b]Determined by HPLC analysis (Chiralcel OD-H).
[c]Absolute configuration determined by comparison of optical rotation to literature values.
[d]Yield after chromatography.
[e]Determined prior to decarboxylation.

Alkyl-substituted alkenes (R=alkyl) are challenging to purify due to minor amounts of non-selective cyclization. Because the Knoevenagel and conjugate addition reactions are both performed in toluene, these reactions can be merged in a tandem procedure (eq. 4). For instance, the combination of 18, hydrocinnamaldehyde (19), acetic acid, piperidine and I in the presence of molecular sieves in toluene at room temperature affords the natural product flindersiachromanone (20) in 80% ee and 77% overall yield after decarboxylation with p-TsOH. (The use of catalyst III instead of I affords lower enantioselectivity at 23° C., the temperature required for the Knoevenagel reaction.)

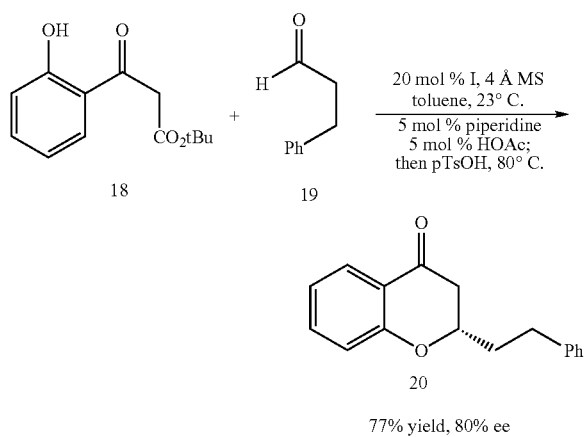

(4)

77% yield, 80% ee

Without limitation, it appears this reaction invokes hydrogen bonding between the β-ketoester substrate and chiral thiourea. The interaction between the quinuclidine nitrogen and phenol then promotes the selective intramolecular conjugate addition. Tertiary amine and thiourea functional groups together in a single catalyst deliver high selectivity. For example, quinine as a catalyst for the reaction (20 mo 1%) results in low enantioselectivity (17% ee) and the bis-(3,5-CF$_3$phenyl)thiourea alone does not promote cyclization when combined with 5 in toluene. Additionally, the combination of 20 mol % each of quinine and bis-(3,5-CF$_3$phenyl)thiourea affords only 23% ee of 6.

As illustrated in the examples provided below, the invention provides an enantioselective method for the synthesis of flavanones and chromanones, and, more specifically, an example of a bifunctional quinine-derived thiourea catalyst activating a β-ketoester alkylidene substrate and promoting a conjugate addition of a phenol to deliver enantioenriched flavanones and chromanones.

Various other embodiments of this invention can be used to provide the first asymmetric syntheses of the natural (S)-abyssinones I, II, III, and IV 4'-OMe (21a-d) and the corresponding enantiomers. This achievement has led to the discovery that compounds from this natural product class regulate matrix metalloproteinase expression and inhibit tumor cell growth in a stereo-dependent manner.

The synthetic approach is outlined in Scheme 2, with application of the asymmetric thiourea-catalyzed cyclization described above, to provide controlled access to either stereoisomer of these natural products. The successful execution of this approach is in part related to the identification of mild decarboxylation/deprotection conditions in order to maintain the integrity of the newly formed C2 stereocenter. A Knoevenagel condensation between an appropriately protected β-keto ester 25 and different aldehydes (24) corresponding to each abyssinone provides an alkylidene poised for thiourea-catalyzed cyclization. It was thought that efficiency could be maximized if, optionally, the decarboxylation and unmasking of the C7 phenol were performed in a single flask as the last step.

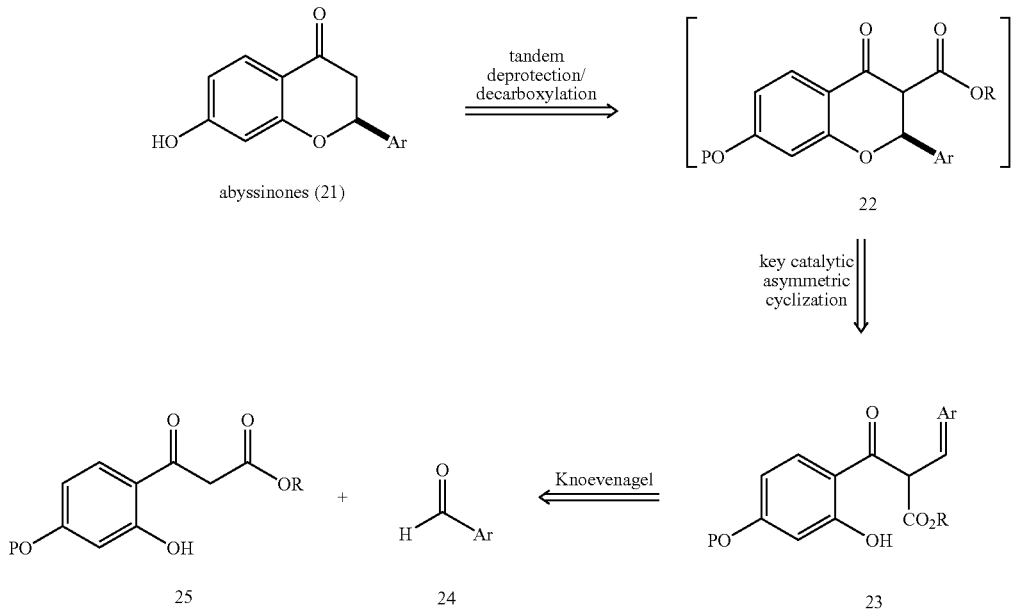

The four aldehydes (24a-d) were prepared efficiently from 4-hydroxybenzaldehyde for condensation with β-keto esters under standard Knoevenagel conditions (e.g., piperidinium acetate, Dean-Stark). These reactions produced the desired alkylidenes (23), but also significant amounts of racemic cyclization adducts (±22). After surveying various conditions, it was found that bis-morpholine aminals (28a-d), used directly without purification, underwent smooth Knoevenagel condensation with various β-ketoesters (3 equiv of glacial acetic acid at 22° C. in toluene) to deliver 23 with minimal levels of racemic cyclized compounds (Scheme 3).

Scheme 3.
Knoevenagel Condensation

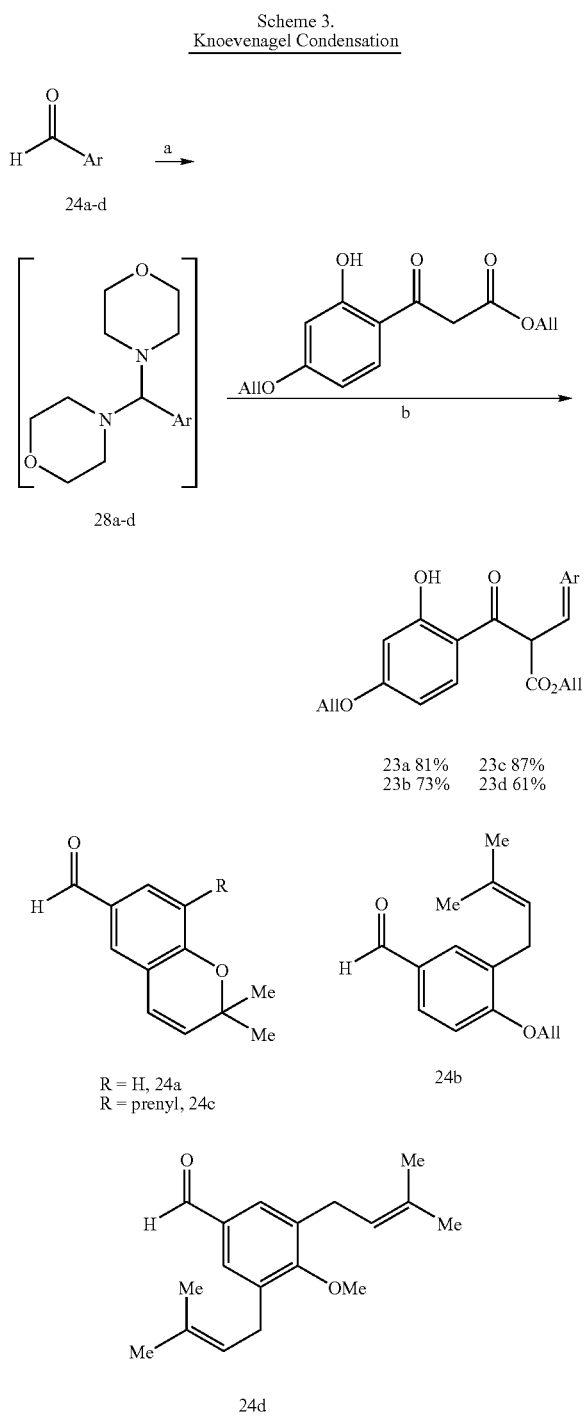

Conditions:
(a) morpholine, benzene, Dean Stark, 110° C. 97-99%;
(b) HOAc, PhMe, 22° C.

Initially, various O-aryl-protected t-butyl esters (e.g., 25, R=t-Bu) were employed, but these products could not be converted into the corresponding abyssinones without significant racemization or functionalization of the abyssinones containing prenyl side chains. In response to this observation, the allyl phenyl ether and allyl ester combination (25a) was used. This bis-allyl protection approach afforded the desired alkylidene ketoesters (23a-d) and set the stage for the decarboxylation and phenol deprotection to be performed in one flask to deliver the target molecules.

Asymmetric cyclizations with 23a-d were catalyzed by exposure to 10 mol % of either the quinine or quinidine-derived thiourea IV or V at −25° C. in toluene (Table 3). (Marcelli, T.; van der Haas, R. N. S.; van Maarseveen, J. H.; Hiemstra, H. *Angewandte Chemie-International Edition* 2006, 45, 929-931. For recent reviews of thiourea catalysis, see: (a) Takemoto, Y. Org. Biomol. Chem. 2005, 3, 4299-4306. (b) Taylor, M. S.; Jacobsen, E. N. Angew. Chem. Int. Ed. 2006, 45, 1520-1543. (c) Connon, S. J. Chem. Eur. J. 2006, 12, 5418-5427. (d) Connon, S. J. Chem. Commun. 2008, 2499-2510.) For the limited applications of thiourea catalysis in total synthesis, see: (a) Hoashi, Y.; Yabuta, T.; Takemoto, Y. Tetrahedron Lett. 2004, 45, 9185-9188. (b) Kanemitsu, T.; Yamashita, Y.; Nagata, K.; Itoh, T. Synlett 2006, 10, 1595-1597. (c) Morokuma, K.; Taira, Y.; Uehara, Y.; Shibahara, S. Keisuke, T.; Ishihara, J.; Hatakeyama, S. Tetrahedron Lett. 2008, 49, 6043-6045.) After consumption of the starting phenols, the corresponding cyclized allyl ester adducts 22a-d were isolated after simple filtration through silica gel. The $^1$H NMR spectra of these products after cyclization indicated that both the cis and trans isomers, as well as enol tautomers, were present.

TABLE 3
Abyssinone Syntheses

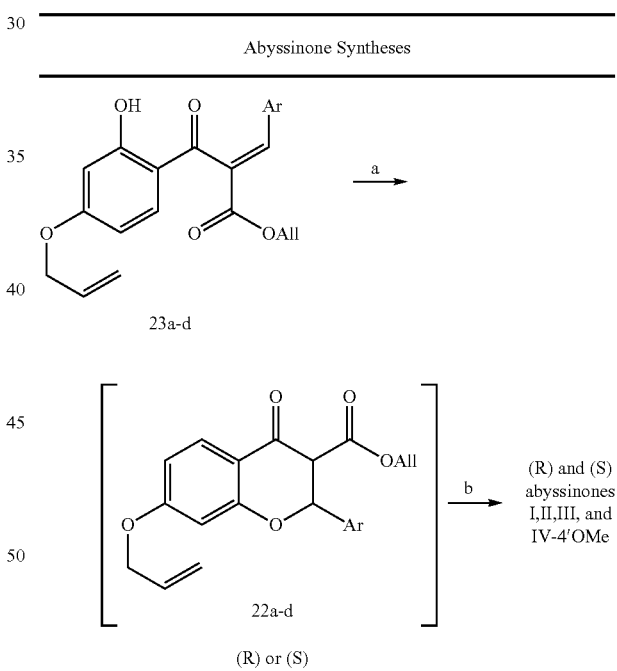

| entry | catalyst | alkene | ee (%)[c] | yield (%)[d] | product | |
|---|---|---|---|---|---|---|
| 1 | IV | 27a | 87 | 70 | (R)-21a | ent-abys. I |
| 2 | V | 27a | 82 | 76 | (S)-21a | abys. I |
| 3 | IV | 27b | 88 | 61 | (R)-21b | ent-abys. II |
| 4 | V | 27b | 89 | 72 | (S)-21b | abys. II |
| 5 | IV | 27c | 86 | 75 | (R)-21c | ent-abys. III |
| 6 | V | 27c | 84 | 70 | (S)-21c | abys. III |

TABLE 3-continued

Abyssinone Syntheses

| 7 | IV | 27d | 95 | 65 | (R)-21d | ent-abys. IV 4'-OMe |
|---|----|-----|----|----|---------|---------------------|
| 8 | V  | 27d | 94 | 65 | (S)-21d | abys. IV 4'-OMe     |

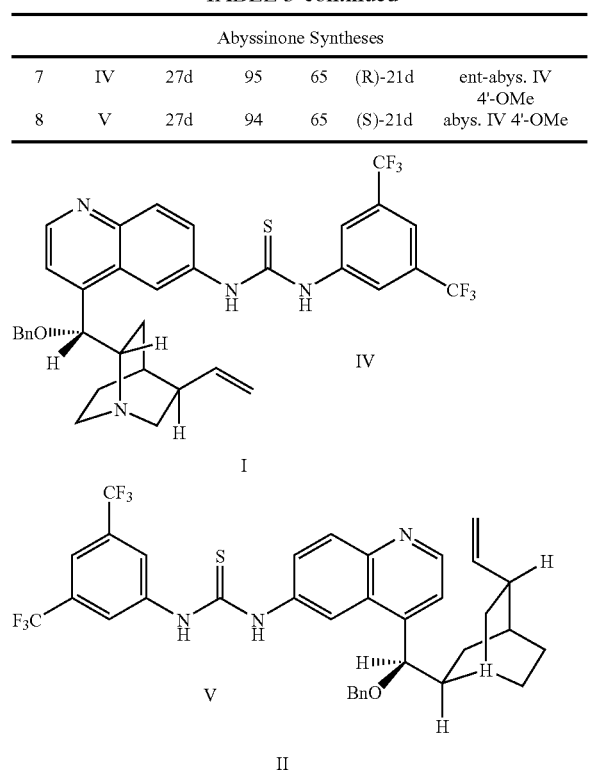

Conditions:
a10 mol % catalyst I or II, −25° C., 0.1 M or 3 in toluene.
bPd(PPh3)4, morpholine, THF, 22° C.
cDetermined by HPLC analysis (Chiralcel OD-H or AD-H).
dIsolated yield over two steps.

Morpholine in the presence of 5 mol % Pd(0) promoted the deprotection and decarboxylation at room temperature to afford all of the natural product (S)-abyssinones I, II, III and IV 4'-OMe ether cleanly and with high yields. (All spectroscopic data (1H, 13C, IR, MS, [α]) of the synthetic abyssinones matched the values reported for the natural products.) The levels of enantioenrichment for each compound from the asymmetric conjugate addition (i.e., 23 to 22) were uniformly excellent. The quinidine-derived thiourea catalyst V provided each of the abyssinones (after deprotection/decarboxylation) with the naturally occurring configuration at C2, while employing the quasi-enantiomeric thiourea IV generated the unnatural abyssinones with comparable levels of stereoselectivity. (The absolute configurations of synthetic 1a-d were determined using CD spectroscopy and matched those reported for natural abyssinones, see ref. 1 and Gaffield, W. Tetrahedon 1970, 26, 4093-4108.) The good overall yields for this process (conjugate addition, allyl deprotection, decarboxylation) provide an efficient method for the construction of optically active flavanones.

The optically enriched abyssinone natural products and their corresponding enantiomers were considered for possible differential biological activity in a therapeutically relevant context. Members of the broad flavanoid family of natural products (over 5000) inhibit the activity and down-regulate the expression of matrix metalloproteinase type 2 (MMP-2) in a variety of tumor cells. However, these studies have focused primarily on achiral isoflavones and none to date have been conducted on the abyssinone family of flavanone natural products.

In the United States, prostate cancer (PCa) is the second most common cause of cancer-related death in men, and mortality is caused by the development of metastatic disease. In order to metastasize, PCa cells must move from the prostate gland to distant sites in the body and continue their unchecked growth. Proteases such as MMPs increase cell invasion, and thus their synthesis by cancer cells facilitates movement and metastatic behavior. The MMP-2 subtype has been shown to be particularly important in human PCa since increased expression in tissue leads to higher rates of metastasis. While several potential MMP inhibitors have been effective in preclinical models, none have been successful in subsequent clinical trials. An alternative strategy for counteracting the pro-invasive effects of MMP-2 focuses on controlling the amount of this enzyme present in tumor cells. This type of approach has been validated by numerous studies which have demonstrated that decreasing the levels of MMP-2 mRNA transcript within cancer cells leads to decreased invasive potential and metastasis. It has been shown that PCa cells treated with the isoflavone genistein have decreased levels of both MMP-2 gene transcript and protein, which leads to an overall reduction in invasive potential. Furthermore, studies performed in additional cancer cell lines have demonstrated that siRNA knockdown of MMP-2 leads to a reduction of both invasion and tumor-induced angiogenesis. Thus, it was sought to evaluate the abyssinones' ability to down-regulate the expression of MMP-2, since this type of intervention could both attenuate/prevent metastasis and, increase survival rates for PCa.

Figure 2A:
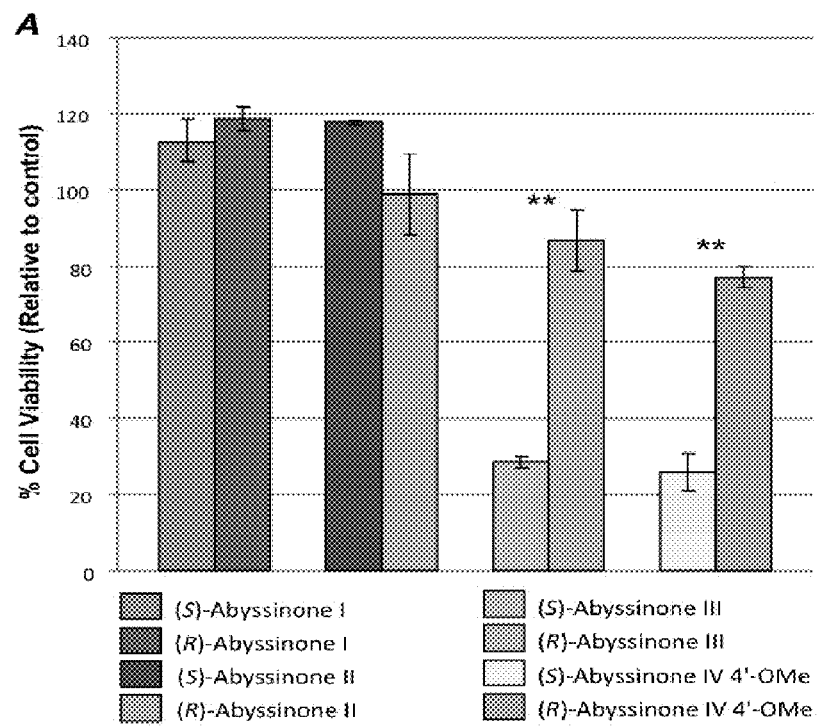
FIG. 2A. Cytotoxicity of abyssinones against C3-M cells at 25 μM.
Figure 2B:
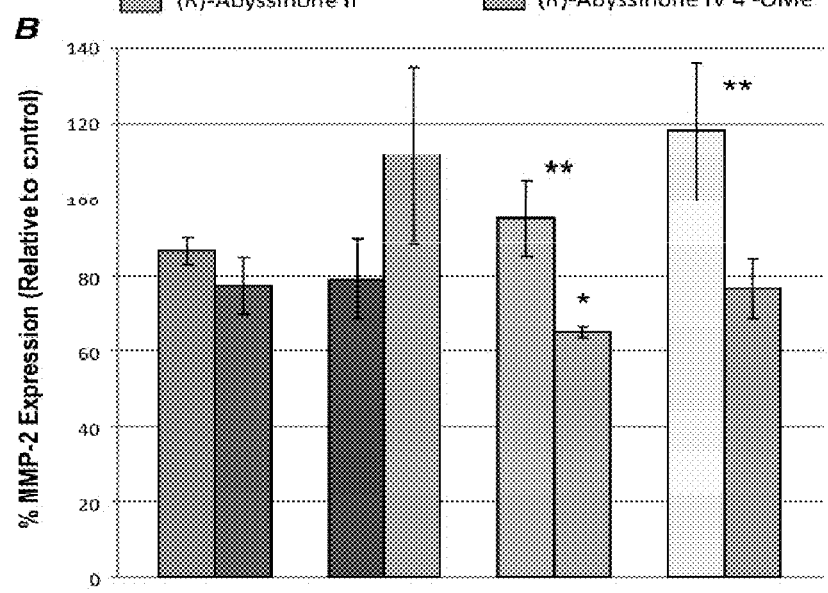
FIG. 2B. MMP-2 expression levels of abyssinone-treated PC3-M cells at 3 μM. N=3 separate experiments, each performed in duplicate. for a description of * (t-tests), see ref. 37.

These studies began by evaluating the impact of optically enriched abyssinones (I, II, III, IV 4'-OMe) on metastatic PCa (PC3-M) cell growth. Given that the abyssinone natural products have never been synthesized in an enantioenriched form, it was thought to determine if the enantiomers of each compound demonstrated differential biological activity against the PCa cell lines. Furthermore, these cytotoxicity studies were instrumental for defining non-toxic levels of 21a-d, which guided the MMP-2 transcript expression evaluations (Compounds from Table 2 were used for biological studies after purification and were all >82% ee.) Metastatic variant human PC3-M cells were treated for 3 days with 0-50 μM of (R)- and (S)-21a-d (eight compounds total) under conditions of exponential cell growth, and then MTT assays were performed. (Control cells were treated with DMSO. See, E.; Neckers, L.; Takimoto, C.; Curt, G.; Bergan, R. C. Mol. Pharmacol. 1997, 51, 193-200 for details.) Under these conditions, low concentrations had minimal effect, at 25 μM differential effects were optimally pronounced, and a further increase to 50 μM was highly toxic. Importantly, the natural and unnatural enantiomers of abyssinones III (21c) and IV 4'-OMe (21d), at 25 μM, displayed statistically different levels of cytotoxicity (FIG. 2). Specifically, (S)-21c and (S)-21d both inhibited cell growth by >70%, relative to control. Although the dose level (25 μM) required for this analysis was clearly not optimized for potency, these results are still indicative of the potential of further studies designed to improve cytotoxicity. Furthermore, these findings, along with the results for abyssinones I and II, highlight the importance of the present enantioselective synthetic method, since this information could not have been obtained without sufficient amounts of the enantioenriched compounds for analysis.

In order to corroborate the biological relevance of stereochemistry, the effects of (R)- and (S)-21a-d (eight compounds total) were evaluated on MMP-2 expression. Levels of MMP-2 transcript were evaluated given that several members of the flavanoid family of natural products have been shown to downregulate the expression of this important prometastatic enzyme, and to determine not only the cytotoxicity profile for these compounds, but also to evaluate their ability to downregulate markers of aggressive disease. Cells were treated with each compound at 3 µM for 3 days, since this dose was not associated with cytotoxicity by MTT assay. This non-toxic dose was chosen for analysis as a means to eliminate any confounding results that could have been obtained as a result of cell death and non-specific downregulation of transcription. After abyssinone exposure, MMP-2 transcript levels were measured by isolating RNA and performing quantitative real-time reverse transcription PCR (qRT-PCR). As a negative control, GAPDH (glyceraldehyde-3-phosphate dehydrogenase) levels were also measured for both the treated and untreated cells. This protein is stably expressed at high levels in most biological systems, and therefore should not be affected by various drug treatments. The GAPDH expression levels were the same for both the treated and untreated cells, which indicated that the effects on MMP-2 expression were not a result of non-specific downregulation of transcription. As in the cell growth studies above, the abyssinone enantiomers exhibit statistically significant differential biological activity (FIG. 2). In particular, for both abyssinones III and IV 4'-OMe, the (R) enantiomers suppress MMP-2 expression to 60-80% of control levels at a non-toxic concentration (3 µM). Interestingly, (R)-enantiomer downregulation is significantly greater than that of the corresponding (S)-enantiomer.

The in vivo biological assays described above interrogate distinctly different functions and highlight the importance of successfully installing the stereochemical elements during the syntheses of the abyssinones. The cytotoxicity and MMP-2 studies conducted with each enantiomer show different response profiles across the abyssinones (21a-d), with promising abilities to differentially target cell growth and metastatic potential. These results indicate the importance of this enantioselective method for accessing the natural and unnatural products. These combined experiments are a full integration of catalytic asymmetric methodology, synthetic application and chemical biology discovery with clinical relevance.

EXAMPLES OF THE INVENTION

The following non-limiting examples and data illustrate various aspects and features relating to the compounds and/or methods of the present invention, including the preparation of enantiomerically-enriched absyssinone compounds, as are available through the asymmetric synthetic methodologies described herein. In comparison with the prior art, the present methods and compounds provide results and data which are surprising, unexpected and contrary thereto. While the utility of this invention is illustrated through the use of several starting materials and chiral thiourea catalyst compounds which can be used therewith, it will be understood by those skilled in the art that comparable results are obtainable with various other starting materials, chiral catalyst compounds and resulting chromanone and/or flavanone compounds, as are commensurate with the scope of this invention.

General Information

All reactions were carried out under a nitrogen atmosphere in flame-dried glassware with magnetic stirring. Toluene was purified by passage through a bed of activated alumina. Reagents were purified prior to use unless otherwise stated following literature guidelines. Purification of reaction products was carried out by flash chromatography using EM Reagent silica gel 60 (230-400 mesh). Analytical thin layer chromatography was performed on EM Reagent 0.25 mm silica gel 60-F plates. Visualization was accomplished with UV light and ceric ammonium nitrate stain followed by heating. Infrared spectra were recorded on a Perkin Elmer 1600 series FT-IR spectrometer. $^1$H-NMR spectra were recorded on a Varian Inova 500 (500 MHz) spectrometer and are reported in ppm using solvent as an internal standard (CDCl$_3$ at 7.26 ppm). Data are reported as (ap=apparent, s=singlet, d=doublet, t=triplet, q=quartet, m=multiplet, b=broad; coupling constant(s) in Hz; integration. Proton-decoupled $^{13}$C-NMR spectra were recorded on a Varian Inova 500 (125 MHz) spectrometer and are reported in ppm using solvent as an internal standard (CDCl$_3$ at 77.0 ppm). Mass spectra data were obtained on a Varian 1200 Quadrupole Mass Spectrometer and Micromass Quadro II Spectrometer.

Thiourea catalyst I was prepared according to the procedure of Soós. Vakulya, B.; Varga, S.; Csampai, A.; Soos, T. *Org. Lett.* 2005, 7, 1967-1969. Thiourea catalyst II was prepared according to the procedure of Takemoto. Okino, T.; Hoashi, Y.; Takemoto, Y. *J. Am. Chem. Soc.* 2003, 125, 12672-12673. Thiourea catalyst III was prepared according to the procedure of Hiemstra. Marcelli, T.; van der Haas, R. N. S.; van Maarseveen, J. H.; Hiemstra, H. *Angew. Chem., Int. Ed.* 2006, 45, 929-931.

General Procedure to Access tert-Butyl 3-(2-hydroxyphenyl)-3-oxopropanoates (18)

Example 1

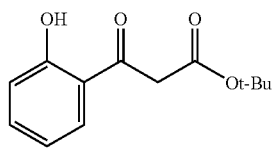

tert-butyl 3-(2-hydroxyphenyl)-3-oxopropanoate (18): To a N$_2$ purged 250 mL RBF is added 30 mL of THF and diisopropylamine (12.0 mL, 86 mmol). The solution is cooled to −78° C. and nBuLi (50 mL, 1.6 M) is added and the solution is warmed to 0° C. for 45 min. The solution is cooled to −78° C. and t-butyl acetate (7.1 mL, 53 mmol) in 12 mL THF is added dropwise over 10 minutes. After 90 min., ethyl salicylate (2.2 mL, 15 mmol) in 15 mL of THF is added. The solution is allowed to warm to RT overnight and quenched with 90 mL of aq. NH$_4$Cl (sat.), extracted with EtOAc (2×25 mL), washed brine (40 mL), dried Na$_2$SO$_4$, filtered, concentrated in vacuo. Purified via column chromatography (silica gel, 10% EtOAc/hex) to give 2.65 g of pale yellow oil (75% yield). IR (film) 2980.2; 2934.9; 1733.6; 1643.7; 1146.6; 757.0 cm$^{-1}$; $^1$H NMR (500 MHz, CDCl$_3$) δ 11.93 (s, 1H); 7.68 (d, J=7.9 Hz, 1H); 7.51 (t, J=7.3, 1H); 7.01 (d, J=8.2 Hz, 1H); 6.93 (t, J=7.3 Hz, 1H); 3.93 (s, 2H); 1.47 (s, 9H); $^{13}$C NMR (125 MHz, CDCl$_3$) δ 198.7, 165.8, 162.3, 136.6, 130.3, 118.8, 118.7, 118.3, 82.1, 46.9, 27.6; LRMS (electrospray): Mass calculated for C$_{13}$H$_{16}$O$_4$, [M]$^+$, 236.10. Found, [M+23]$^+$259.5.

Example 2

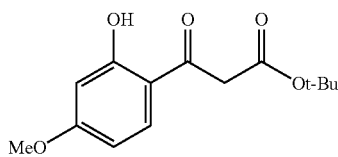

tert-butyl 3-(2-hydroxy-4-methoxyphenyl)-3-oxopropanoate: Prepared according to above procedure using diisopropylamine (8.0 mL, 58 mmol), nBuLi (34 mL, 1.6 M), tert-butyl acetate (4.7 mL, 35 mmol), methyl 4-methoxysalicylate (1.83 g, 10 mmol) yielding 2.04 g (76%) as white needles. mp=40-42° C.; IR (film) 2978.7; 2936.4; 1731.9; 1633.5; 1357.0; 1129.3 cm$^{-1}$; $^1$H NMR (500 MHz, CDCl$_3$) δ 12.42 (s, 1H); 7.57 (d, J=9.0 Hz, 1H); 6.45 (d, J=9.0, 1H); 6.44 (s, 1H); 3.85 (s, 3H); 3.84 (s, 2H); 1.46 (s, 9H); $^{13}$C NMR (125 MHz, CDCl$_3$) δ 197.1, 166.7, 166.6, 165.9, 132.3, 113.5, 108.3, 101.2, 82.5, 55.9, 47.2, 28.2; LRMS (electrospray): Mass calculated for C$_{14}$H$_{18}$O$_5$, [M]$^+$, 266.12. Found [M+23]$^+$, 289.5.

Example 3

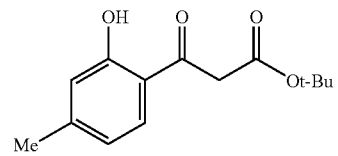

tert-butyl 3-(2-hydroxy-4-methylphenyl)-3-oxopropanoate: Prepared according to above procedure using diisopropylamine (3.8 mL, 28 mmol), nBuLi (21 mL, 1.2 M), tert-butyl acetate (2.1 mL, 16 mmol), 2-hydroxy-4-methylbenzoyl chloride (5 mmol, prepared from 760 mg 4-methylsalicylic acid and SOCl$_2$, 1.2 mL, heated to 47° C. in 12 mL toluene for 4 h) yielding 327 mg (26%) as white needles. mp=88-90° C.; IR (film) 1733.8; 1652.6; 1145.0 cm$^{-1}$; $^1$H NMR (500 MHz, CDCl$_3$) δ 11.95 (s, 1H); 7.54 (d, J=8.2 Hz, 1H); 6.81 (s, 1H); 6.72 (d, J=8.2, 1H); 3.88 (s, 2H); 2.36 (s, 3H); 1.45 (s, 9H); $^{13}$C NMR (125 MHz, CDCl$_3$) δ 198.5, 166.5, 163.0, 148.9, 130.5, 120.7, 118.8, 117.2, 82.6, 47.4, 28.1, 22.2; LRMS (electrospray): Mass calculated for C$_{14}$H$_{18}$O$_4$, [M]$^+$, 250.12. Found [M+23]$^+$, 272.9.

Example 4

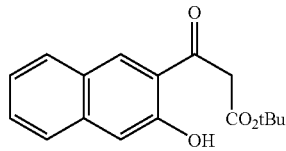

tert-butyl 3-(3-hydroxynaphthalen-2-yl)-3-oxopropanoate: Prepared according to above procedure using diisopropylamine (2.0 mL, 15 mmol), nBuLi (11.4 mL, 1.2 M), tert-butyl acetate (3.4 mL, 12 mmol), 3-hydroxynaphthalene-2-carbonyl chloride (3.9 mmol, prepared from 730 mg of 3-hydroxy-2-naphthoic acid and SOCl$_2$, 0.9 mL, heated to 40° C. in 9 mL toluene for 4 h) yielding 666 mg (57%) as yellow needles. mp=80-84° C.; IR (film) 2981.9; 2919.0; 1732.1; 1642.5; 1261.4; 1147.6 cm$^{-1}$; $^1$H NMR (500 MHz, CDCl$_3$) δ 11.17 (s, 1H); 8.29 (s, 1H); 7.78 (d, J=8.0 Hz, 1H); 7.65 (d, J=8.2 Hz, 1H); 7.50 (t, J=7.0, 1H); 7.33-7.27 (m, 2H); 4.05 (s, 2H); 1.42 (s, 9H); $^{13}$C NMR (125 MHz, CDCl$_3$) δ 199.3, 166.2, 157.2, 138.5, 133.7, 130.2, 129.6, 127.1, 126.5, 124.5, 120.9, 112.7, 82.9, 47.8, 28.1; LRMS (electrospray): Mass calculated for C$_{17}$H$_{18}$O$_4$, [M]$^+$, 286.12. Found [M]$^+$, 285.8.

Example 5

Two general procedures were followed for the synthesis of alkene substrates: General Procedure A for the preparation of alkylidene substrates: To a 25 mL RBF was added tert-butyl 3-(2-hydroxyphenyl)-3-oxopropanoate 18 (618 mg, 2.6 mmol), benzaldehyde (265 μL, 2.6 mmol) 12.0 mL benzene, piperidine (13 μL, 0.13 mmol) and glacial acetic acid (7.5 μL, 0.13 mmol). The flask was equipped with a Dean-Stark trap and water condenser and heated to reflux. The reaction was allowed to cool to RT, taken up in EtOAc (40 mL) and washed with brine (25 mL). The organic layer was dried with Na$_2$SO$_4$, filtered concentrated to give a yellow oil which was recrystallized from hexanes/CH$_2$Cl$_2$.

Example 6

General Procedure B for the preparation of alkylidene substrates: To a 25 mL RBF was added tert-butyl 3-(2-hydroxyphenyl)-3-oxopropanoate (18) (259 mg, 1.1 mmol), 2-naphthaldehyde (172 mg, 1.1 mmol) and Na$_2$SO$_4$ (2.34 g, 16.5 mmol). The flask was purged with N$_2$. Toluene (12 mL) and piperidinium acetate (0.025 M in toluene, 2.2 mL) were added and the heterogenous mixture was stirred at RT for 7 d. The reaction was taken up in EtOAc (40 mL) and washed with brine (25 mL). The organic layer was dried with Na$_2$SO$_4$, filtered concentrated to give a tan oil which was recrystallized from hexanes/CH$_2$Cl$_2$.

Example 7

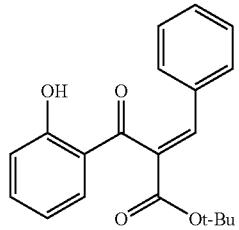

(E)-tert-butyl 2-(2-hydroxyphenylcarbonyl)-3-phenylprop-2-enoate (5): Prepared according to general procedure A using tert-butyl 3-(2-hydroxyphenyl)-3-oxopropanoate (18) (618 mg, 2.6 mmol), benzaldehyde (265 μL, 2.6 mmol), 12.0 mL benzene, piperidine (13 μL, 0.13 mmol) and glacial acetic acid (7.5 μL, 0.13 mmol), refluxed for 2 h. Purified via recrystallization from hexanes/CH$_2$Cl$_2$, yielding 708 mg (83%) of 5 as clear crystals. mp=109-110° C.; IR (film) 2978.4; 1737.4; 1692.4; 1643.3; 1145.8 cm$^{-1}$; $^1$H NMR (500 MHz, CDCl$_3$) δ 11.92 (bs, 1H), 7.86 (s, 1H), 7.55 (d, J=8.0 Hz, 1H), 7.49 (t, J=8.4 Hz), 1H, 7.37-7.28 (m, 5H), 7.04 (d, J=8.4 Hz. 1H), 6.83 (t, J=7.3 Hz, 1H), 1.42 (s, 9H); $^{13}$C NMR (125 MHz, CDCl$_3$) δ 201.6, 163.8, 162.8, 142.3, 137.2, 133.0, 131.9, 131.6, 130.7, 130.3, 129.1, 120.2, 119.6, 118.5, 82.8, 28.1; LRMS (electrospray): Mass calculated for C$_{20}$H$_{20}$O$_4$, [M]$^+$, 324.13. Found [M+23]$^+$, 347.3. An NOE difference experiment was conducted for this compound and a positive NOE was seen for the alkene proton when the tert-butyl signal was irradiated and a positive NOE was seen for the tert-butyl signal upon irradiation of the alkene proton.

Example 8

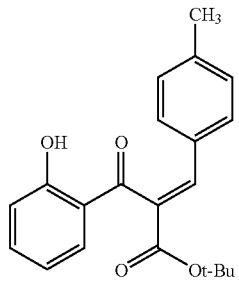

(E)-tert-butyl 2-(2-hydroxyphenylcarbonyl)-3-p-tolyl-prop-2-enoate: Prepared according to general procedure A using tert-butyl 3-(2-hydroxyphenyl)-3-oxopropanoate (18) (354 mg, 1.5 mmol), p-tolualdehyde (150 μL, 1.5 mmol), 15.0 mL benzene, piperidine (15 μL, 0.15 mmol) and glacial acetic acid (8.6 μL, 0.15 mmol), refluxed for 3 h. Purified via recrystallization from hexanes/CH$_2$Cl$_2$, yielding 350 mg (69%) of clear prisms. mp=86-89° C.; IR (film) 2978.2; 1712.8; 1624.5; 1155.2 cm$^{-1}$; $^1$H NMR (100.7 MHz, CDCl$_3$) δ 11.93 (bs, 1H), 7.82 (s, 1H), 7.52 (d, J=8.0 Hz, 1H), 7.48 (t, J=8.2 Hz, 1H), 7.25-7.08 (AA'BB', 4H), 7.03 (d, J=8.2 Hz, 1H), 6.81 (t, J=7.6 Hz, 1H), 2.30 (s, 3H), 1.40 (s, 9H); $^{13}$C NMR (125 MHz, CDCl$_3$) δ 202.0, 163.9, 162.8, 142.3, 141.3, 137.1, 131.9, 130.4 (x2), 130.1, 129.9, 120.2, 119.5, 118.4, 82.6, 28.1, 21.6; LRMS (electrospray): Mass calculated for C$_{21}$H$_{22}$O$_4$, [M]$^+$, 338.14. Found [M+23]$^+$, 361.4.

Example 9

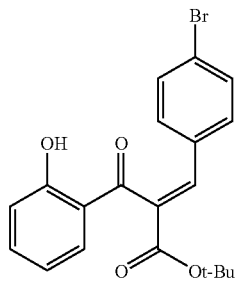

(E)-tert-butyl 3-(4-bromophenyl)-2-(2-hydroxyphenylcarbonyl)prop-2-enoate: Prepared according to general procedure A using tert-butyl 3-(2-hydroxyphenyl)-3-oxopropanoate (18) (289 mg, 1.2 mmol), 4-bromobenzaldehyde (226 mg, 1.2 mmol), 20.0 mL benzene, piperidine (10 μL, 0.1 mmol) and glacial acetic acid (5.6 μL, 0.1 mmol), refluxed for 3 h. Purified via recrystallization from hexanes/CH$_2$Cl$_2$, yielding 278 mg (57%) of clear crystals. mp=98-100° C.; IR (film) 2978.4; 1712.8; 1629.0; 1155.7 cm$^{-1}$; $^1$H NMR (500 MHz, CDCl$_3$) δ 11.84 (bs, 1H); 7.78 (s, 1H); 7.52-7.48 (m, 2H); 7.43-7.21 (AA'BB', 4H); 7.04 (d, J=7.0 Hz, 1H); 6.83 (t, J=7.3 Hz, 1H); 1.41 (s, 9H); $^{13}$C NMR (125 MHz, CDCl$_3$) δ 201.3, 163.5, 162.9, 140.8, 137.4, 132.5, 132.3, 131.9, 131.8, 131.6, 125.3, 120.0, 119.7, 118.7, 83.1, 28.1; LRMS (electrospray): Mass calculated for C$_{20}$H$_{19}$BrO$_4$, [M]$^+$, 402.1, 404.0. Found [M+23]$^+$, 424.7, 426.8. An NOE difference experiment was conducted for this compound and a positive NOE was seen for the alkene proton when the tert-butyl signal was irradiated and a positive NOE was seen for the tert-butyl signal upon irradiation of the alkene proton. This compound was further characterized by X-ray crystal structure, see S56.

Example 10

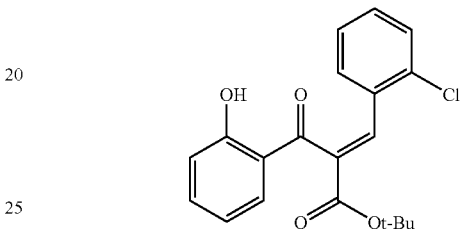

(E)-tert-butyl 3-(2-chlorophenyl)-2-(2-hydroxyphenylcarbonyl)prop-2-enoate: Prepared according to general procedure A using tert-butyl 3-(2-hydroxyphenyl)-3-oxopropanoate (18) (236 mg, 1.0 mmol), 2-chlorobenzaldehyde (113 μL, 1.0 mmol) 15 mL benzene, piperidine (10 μL, 0.1 mmol) and glacial acetic acid (5.6 μL, 0.1 mmol), refluxed for 90 min. Purified via recrystallization from hexanes/CH$_2$Cl$_2$, yielding 72 mg (20%) of a white solid. mp=75-78° C. IR (film) 2979.0; 1720.5; 1630.9; 1156.3 cm$^{-1}$; $^1$H NMR (500 MHz, CDCl$_3$) δ 11.80 (bs, 1H); 8.19 (s, 1H); 7.50 (d, J=7.9 Hz, 1H); 7.44 (t, J=7.9 Hz, 1H); 7.36 (d, J=7.9 Hz, 1H); 7.26 (d, J=7.9 Hz, 1H); 7.21 (t, J=7.6 Hz, 1H); 7.08 (t, J=7.06, Hz, 1H); 6.97 (d, J=7.9 Hz, 1H); 6.82 (t, J=7.6 Hz, 1H); 1.43 (s, 9H); $^{13}$C NMR (125 MHz, CDCl$_3$) δ 200.6, 163.3, 162.8, 139.1, 137.2, 135.0, 134.0, 131.9 (double intensity), 131.3, 130.2, 130.1, 127.2, 120.0, 119.5, 118.5, 83.1, 28.1; LRMS (electrospray): Mass calculated for C$_{20}$H$_{19}$ClO$_4$ [M]$^+$, 358.09. Found [M+23]$^+$, 381.5.

Example 11

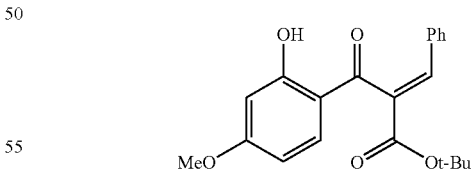

(E)-tert-butyl 2-(2-hydroxy-4-methoxyphenylcarbonyl)-3-phenylprop-2-enoate: Prepared according to general procedure A using tert-butyl 3-(2-hydroxy4-methoxyphenyl)-3-oxopropanoate (532 mg, 2.0 mmol), benzaldehyde (200 μL, 2.00 mmol), 12.0 mL benzene, piperidine (10 μL, 0.10 mmol) and glacial acetic acid (5.7 μL, 0.10 mmol), refluxed for 3 h. Purified via recrystallization from hexanes/CH$_2$Cl$_2$, yielding 321 mg (46%) of white solid. mp=105-107° C.; IR (film) 2977.5; 1712.8; 1624.0; 1155.6 cm$^{-1}$; $^1$H NMR (500 MHz, CDCl$_3$) δ 12.41 (bs, 1H), 7.81 (s, 1H), 7.41 (d, J=9.1 Hz, 1H), 7.37-7.25 (m, 5H), 6.46 (d, J=2.1 Hz, 1H), 6.34 (dd, J=8.8, 2.1 Hz, 1H), 3.83 (s, 3H), 1.42 (s, 9H); $^{13}$C NMR (125 MHz, CDCl$_3$) δ 199.4, 166.8, 165.8, 164.0, 141.8, 133.6, 133.1, 131.6, 130.5, 130.3, 129.1, 114.3, 108.4, 101.1, 82.6, 55.8, 28.1; LRMS (electrospray): Mass calculated for C$_{21}$H$_{22}$O$_5$ [M]$^+$, 354.14. Found [M+23]$^+$, 377.5.

Example 12

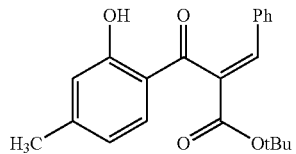

(E)-tert-butyl 2-(2-hydroxy-4-methylphenylcarbonyl)-3-phenylprop-2-enoate: Prepared according to general procedure A using tert-butyl 3-(2-hydroxy-4-methyphenyl)-3-oxopropanoate (250 mg, 1.0 mmol), benzaldehyde (100 μL, 1.00 mmol), 12.0 mL benzene, piperidine (10 μL, 0.10 mmol) and glacial acetic acid (5.7 μL, 0.10 mmol), refluxed for 3 h. Purified via recrystallization from hexanes/CH$_2$Cl$_2$, yielding 154 mg (46%) of white solid. mp=92-95° C.; IR (film) 2977.9; 1718.2; 1627.9; 1155.0 cm$^{-1}$; $^1$H NMR (500 MHz, CDCl$_3$) δ 11.95 (bs, 1H), 7.82 (s, 1H), 7.40 (d, J=9.6 Hz, 1H), 7.36-7.29 (m, 5H), 6.83 (s, 1H), 6.61 (d, J=8.0 Hz, 1H), 2.34 (s, 3H), 1.41 (s, 9H); $^{13}$C NMR (125 MHz, CDCl$_3$) δ 200.8, 163.9, 163.0, 149.0, 142.0, 133.0, 131.8, 131.7, 130.6, 130.3, 129.1, 120.9, 118.5, 118.0, 82.7, 28.1, 22.3; LRMS (electrospray): Mass calculated for C$_{21}$H$_{22}$O$_4$ [M]$^+$, 338.15. Found [M+23]$^+$, 361.2. An NOE difference experiment was conducted for this compound and a positive NOE was seen for the alkene proton when the tert-butyl signal was irradiated and a positive NOE was seen for the tert-butyl signal upon irradiation of the alkene proton.

Example 13

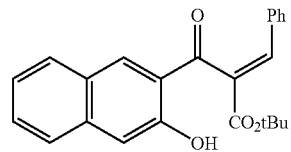

(E)-tert-butyl 2-(3-hydroxynaphthalene-2-carbonyl)-3-phenylprop-2-enoate: Prepared according to general procedure A using tert-butyl 3-(3-hydroxynaphthalen-2-yl)-3-oxopropanoate (286 mg, 1.0 mmol), benzaldehyde (100 μL, 1.00 mmol), 15.0 mL benzene, piperidine (10 μL, 0.10 mmol) and glacial acetic acid (5.7 μL, 0.10 mmol), refluxed for 4 h. Purified via recrystallization from hexanes/CH$_2$Cl$_2$, yielding 213 mg (57%) of yellow solid. mp=132-135° C.; IR (film) 2977.6; 1716.6; 1639.5; 1154.5 cm$^{-1}$; $^1$H NMR (500 MHz, CDCl$_3$) δ 11.20 (bs, 1H), 8.19 (s, 1H); 7.96 (s, 1H); 7.70 (t, J=7.3 Hz, 2H), 7.51 (t, J=8.0 Hz, 1H), 7.40-7.25 (m, 7H), 1.38 (s, 9H); $^{13}$C NMR (125 MHz, CDCl$_3$) δ 201.9, 163.9, 157.1, 142.8, 138.7, 135.1, 132.8, 131.6, 130.8, 130.4, 130.2, 129.8, 129.2, 127.3, 126.6, 124.4, 121.7, 112.6, 83.0, 28.1; LRMS (electrospray): Mass calculated for C$_{24}$H$_{22}$O$_4$ [M]$^+$, 374.15. Found [M+23]$^+$, 397.0.

Example 14

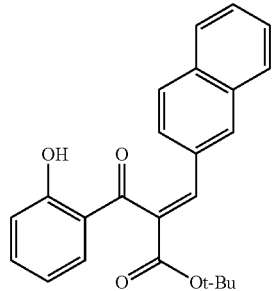

(E)-tert-butyl 2-(2-hydroxyphenylcarbonyl)-3-(naphthalen-2-yl)prop-2-enoate: Prepared according to general procedure B using tert-butyl 3-(2-hydroxyphenyl)-3-oxopropanoate (18) (259 mg, 1.1 mmol), 2-naphthaldehyde (172 mg, 1.1 mmol), 12.0 mL toluene, piperidinium acetate (2.2 mL, 0.025M in toluene) and sodium sulfate (2.3 g), stirred at 22° C. for 7 d. Purified via recrystallization from hexanes/CH$_2$Cl$_2$, yielding 240 mg (58%) of beige crystals. mp=111-112° C.; IR (film) 2978.0; 1712.8; 1624.1; 1154.1 cm$^{-1}$; $^1$H NMR (500 MHz, CDCl$_3$) δ 11.97 (bs, 1H); 8.02 (s, 1H); 7.91 (s, 1H); 7.79 (d, J=7.6 Hz, 1H); 7.78 (d, J=7.3 Hz, 1H); 7.70 (d, J=8.5 Hz, 1H); 7.58 (dd, J=8.0, 2.5 Hz, 1H); 7.51-7.46 (m, 3H); 7.37 (dd, J=8.5, 1.5 Hz, 1H); 7.05 (d, J=8.2 Hz, 1H); 6.81 (t, J=7.3 Hz, 1H); 1.44 (s, 9H); $^{13}$C NMR (125 MHz, CDCl$_3$) δ 201.9, 163.9, 162.9, 142.4, 137.3, 134.1, 133.2, 132.05, 132.03, 131.6, 130.6, 129.0 (x2), 128.0, 127.9, 127.0, 125.9, 120.3, 119.6, 118.6, 82.8, 28.2; LRMS (electrospray): Mass calculated for C$_{24}$H$_{22}$O$_4$ [M]$^+$, 374.14. Found [M+23]$^+$, 397.2.

Example 15

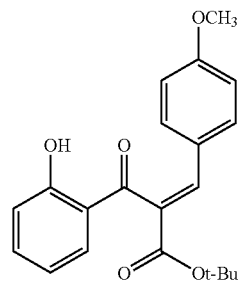

(E)-tert-butyl 2-(2-hydroxyphenylcarbonyl)-3-(4-methoxyphenyl)prop-2-enoate: Prepared according to general procedure B using tert-butyl 3-(2-hydroxyphenyl)-3-oxopropanoate (18) (236 mg, 1.0 mmol), p-anisaldehyde (115 μL, 1.0 mmol), 12.0 mL toluene, piperidinium acetate (0.3 mL, 0.025 M in toluene) and sodium sulfate (2.0 g), stirred at 22° C. for 7 d. Purified via recrystallization from hexanes/CH$_2$Cl$_2$, yielding 250 mg (71%) of white crystals. mp=129-132° C.; IR (film) 2982.5; 1708.9; 1603.8; 1246.8; 1155.0 cm$^{-1}$; $^1$H NMR (500 MHz, CDCl$_3$) δ 11.97 (bs, 1H); 7.80 (s, 1H); 7.56 (d, J=8.0 Hz, 1H); 7.48 (t, J=7.4 Hz, 1H); 7.32-6.79 (AA'BB', 4H), 7.04 (t, J=8.6 Hz, 1H), 6.82 (m, 1H), 3.78 (s, 3H); 1.40 (s, 9H); $^{13}$C NMR (125 MHz, CDCl$_3$) δ 202.3, 164.1, 162.9, 161.6, 142.0, 137.1, 132.4, 132.0, 128.9, 125.3, 120.2, 119.5, 118.5, 114.7, 82.5, 55.6, 28.1; LRMS (electrospray): Mass calculated for $C_{21}H_{22}O_5$ $[M]^+$, 354.14. Found $[M+23]^+$, 377.5. An NOE difference experiment was conducted for this compound and a positive NOE was seen for the alkene proton when the tert-butyl signal was irradiated and a positive NOE was seen for the tert-butyl signal upon irradiation of the alkene proton.

Example 16

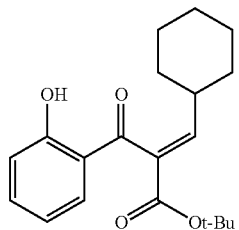

(E)-tert-butyl 3-cyclohexyl-2-(2-hydroxyphenylcarbonyl) prop-2-enoate: Prepared according to general procedure B using tert-butyl 3-(2-hydroxyphenyl)-3-oxopropanoate (18) (236 mg, 1.0 mmol), cyclohexanecarboxaldehyde (120 μL, 1.0 mmol) 7.0 mL benzene, piperidinium acetate (2.0 mL, 0.025M in toluene) and sodium sulfate (2.1 g), stirred at 22° C. for 8 d. Purified via column chromatography with 5% EtOAc/hexanes, yielding 165 mg (50%) of a white solid. $R_f$=0.59 (10% ether/hexanes); mp=62-65° C.; IR (film) 2929.2; 1716.6; 1631.9; 1257.5; 1153.6 cm$^{-1}$; $^1$H NMR (500 MHz, CDCl$_3$) δ 11.92 (s, 1H); 7.51-7.46 (m, 2H); 7.02 (d, J=8.2 Hz, 1H); 6.90-6.86 (m, 2H); 2.11 (m, 1H); 1.68-1.60 (m, 5H); 1.35 (s, 9H); 1.20-1.15 (m, 5H). $^{13}$C NMR (125 MHz, CDCl$_3$) δ 200.8, 163.7, 162.6, 152.2, 136.9, 132.3, 124.6, 120.5, 119.2, 118.4, 82.3, 31.9, 28.5, 28.0, 25.8, 25.1; LRMS (electrospray): Mass calculated for $C_{20}H_{26}O_4$ $[M]^+$, 330.18. Found $[M+23]^+$, 353.6.

Example 17

General Cyclization Procedure

To a 10 mL round bottom flask containing a magnetic stirring bar was added alkylidene compound, 10 mol % thiourea catalyst III. The flask is purged with N$_2$. The solids were dissolved in toluene and the resulting solution was stored at −25° C. Reaction progress was monitored by RP HPLC. After completion of reaction, the solution was diluted with EtOAc (20 mL), poured into a separatory funnel and washed with brine. The organic layer was dried over anhydrous Na$_2$SO$_4$, filtered and concentrated to provide the crude flavanone. The crude mixture was run through a silica gel column (10% EtOAc/hexanes).

Example 18

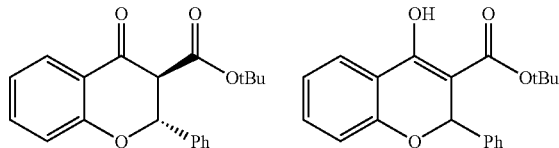

(2R,3S)-t-butyl 4-oxo-2-phenylchroman-3-carboxylate and t-butyl 4-hydroxy-2-phenyl-2H-chromene-3-carboxylate 6: Prepared according to general procedure using (E)-tert-butyl 2-(2-hydroxyphenylcarbonyl)-3-phenylprop-2-enoate 5 (65 mg, 0.2 mmol) and thiourea catalyst III (14 mg, 0.02 mmol) in 2 mL toluene for 36 hours to afford 55 mg (85%) of 6 as a pink solid in 92% ee. Analytical data for 6, $^1$H NMR (500 MHz, CDCl$_3$) δ for trans: 7.95 (d, J=7.3 Hz, 1H), 7.53-7.24 (m, 6H), 7.08 (t, J=7.3 Hz, 1H), 7.03 (d, J=8.3 Hz, 1H), 5.62 (d, J=12.2 Hz, 1H), 3.98 (d J=12.2 Hz, 1H), 1.30 (s, 9H); some enol tautomer may be present, depending on concentration: 12.49 (bs, 1H), 7.66 (d, J=7.3, 1H), 7.53-7.24 (m, 6H) 6.94 (t, J=7.6 Hz, 1H), 6.79 (d, J=8.2 Hz, 1H), 6.18 (s, 1H), 1.42 (s, 9H). $^{13}$C NMR (125 MHz, CDCl$_3$) δ 188.5, 166.2, 161.3, 136.78, 136.76, 129.7, 128.9, 127.9, 127.7, 122.2, 120.3, 118.3, 82.6, 81.8, 60.6, 28.0.

Example 19

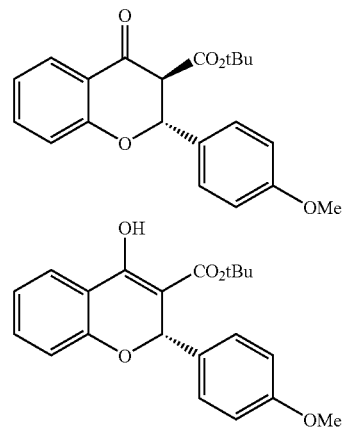

(2R,3S)-t-butyl 4-oxo-2-(4-methoxyphenyl)chroman-3-carboxylate and t-butyl 4-hydroxy-2-4-methoxyphenyl)-2H-chromene-3-carboxylate: Prepared according to general procedure using (E)-tert-butyl 2-(2-hydroxyphenylcarbonyl)-3-phenylprop-2-enoate (27 mg, 0.08 mmol) and thiourea catalyst III (5 mg, 0.008 mmol) in 0.8 mL toluene for 24 hours to afford 25 mg (94%) of a white solid in 91% ee. Analytical data for 12, $^1$H NMR (500 MHz, CDCl$_3$) δ for trans: 7.95 (d, J=7.6 Hz, 1H), 7.50 (t, J=7.9 Hz, 1H), 7.46-6.95 (AA'BB', 4H), 7.06 (t, J=7.3 Hz, 1H), 7.01 (d, J=8.2 Hz, 1H), 5.57 (d, J=12.5 Hz, 1H), 3.98 (d J=12.5 Hz, 1H), 3.82 (s, 3H), 1.32 (s, 9H); enol tautomer: 12.53 (bs, 1H), 7.67 (d, J=7.6, 1H), 7.30-6.79 (AA'BB', 4H) 7.23 (t, J=8.0 Hz, 1H), 6.92 (m, 1H), 6.13 (s, 1H), 3.74, (s, 3H), 1.42 (s, 9H).

Example 20

General Cyclization/Decarboxylation Procedure

To a 10 mL round bottom flask containing a magnetic stirring bar was added alkylidene compound, 10 mol % thiourea catalyst III. The flask is purged with N$_2$. The solids were dissolved in toluene and the resulting solution was stored at −25° C. Reaction progress was monitored by RP HPLC. After complete cyclization, 50 mol % p-toluenesulfonic acid was added to the flask and the solution was heated to 80° C., and the reaction was monitored by TLC. Upon completion of the reaction, the solution was allowed to cool and the solution was diluted with EtOAc (20 mL), poured into a separatory funnel and washed with brine. The organic layer was dried over anhydrous Na$_2$SO$_4$, filtered and concentrated to provide the crude flavanone. The crude mixture was purified via silica gel chromatography (10% EtOAc/hexanes) and concentrated in vacuo.

Example 21

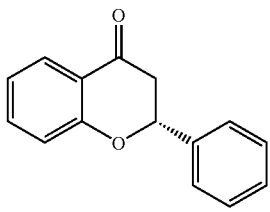

(R)-flavanone (7): Prepared according to general procedure using (E)-tert-butyl 2-(2-hydroxyphenylcarbonyl)-3-phenylprop-2-enoate (5) (65 mg, 0.2 mmol) and thiourea catalyst III (14 mg, 0.02 mmol) in 2.0 mL toluene for 36 h at −25° C. and p-toluenesulfonic acid (19 mg, 0.10 mmol) for 24 h. Purification via column chromatography with 10% EtOAc/hexanes afforded 41 mg (92%) of 7 as a white solid in 94% ee. $[\alpha]_D$: +55.6 (EtOH, c=0.5). Analytical data match those reported in the literature.

Example 22

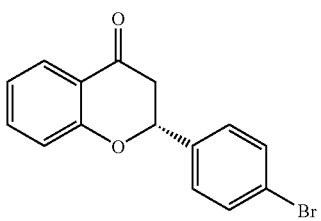

2-(4-bromophenyl)chroman-4-one (8): Prepared according to general procedure using E-tert-butyl 3-(4-bromophenyl)-2-(2-hydroxyphenylcarbonyl)prop-2-enoate (81.0 mg, 0.20 mmol), thiourea catalyst III (14 mg, 0.020 mmol) in 2.0 mL toluene for 38 h at −25° C. and p-toluenesulfonic acid (19 mg, 0.10 mmol) for 36 h. Purification via column chromatography with 10% EtOAc/hexanes afforded 39.5 mg (65%) of 8 as a white solid in 92% ee. mp=115-116° C. $[\alpha]_D$: +50.4 (EtOH, c=0.5). Analytical data for 8: IR (film) 1691.8, 1604.8, 1465.1, 1304.6, 1222.9 cm$^{-1}$; $^1$H NMR (500 MHz, CDCl$_3$) δ 7.93 (d, J=7.5 Hz, 1H), 7.58-7.36 (AA'BB', 4H), 7.52 (t, J=8.0 Hz, 1H), 7.09-7.05 (m, 2H), 5.45 (dd, J=13.2, 2.4 Hz, 1H), 3.00 (dd, J=16.8, 13.3 Hz, 1H), 2.88 (dd, J=16.8, 2.6 Hz, 1H); $^{13}$C NMR (125 MHz, CDCl$_3$) δ 191.7, 161.5, 138.0, 136.6, 132.3, 128.1, 127.3, 123.0, 122.1, 121.1, 118.3, 79.1, 44.8; LRMS (electrospray): Exact mass calcd for C$_{15}$H$_{11}$BrO$_2$ [M]$^+$, 301.99, 303.99. Found [M+1], 305.5.

Example 23

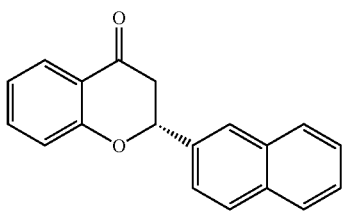

(R)-2-(2-naphthyl)chroman-4-one (9): Prepared according to general procedure using (E)-tert-butyl 2-(2-hydroxyphenylcarbonyl)-3-(naphthalen-2-yl)prop-2-enoate (77 mg, 0.20 mmol), thiourea catalyst III (14 mg, 0.020 mmol) in 2.0 mL toluene for 38 h at −25° C. and p-toluenesulfonic acid (19 mg, 0.10 mmol) for 10 h. Purification via column chromatography with 10% EtOAc/hexanes afforded 49 mg (89%) of 9 as a white solid in 91% ee. $[\alpha]_D$: +56.3 (EtOH, c=0.5). Analytical data for 9: IR (film) 1690.9, 1607.9, 1464.8, 1304.4, 1226.9 cm$^{-1}$; $^1$H NMR (500 MHz, CDCl$_3$) δ 7.99-7.89 (m, 5H), 7.63-7.54 (m, 4H), 7.13-7.09 (m, 2H), 5.68 (dd, J=13.1, 2.4 Hz, 1H), 3.22 (dd, J=16.8, 13.4 Hz, 1H), 3.00 (dd, J=16.8, 2.7 Hz, 1H); $^{13}$C NMR (125 MHz, CDCl$_3$) δ 192.2, 161.8, 136.5, 136.3, 133.6, 133.4, 129.0, 128.4, 128.0, 127.3, 126.8 (x2), 125.6, 123.9, 121.9, 121.2, 118.4, 79.9, 44.9; LRMS (electrospray): Exact mass calcd. for C$_{19}$H$_{14}$O$_2$ [M]$^+$, 274.10. Found [M]$^+$, 273.8.

Example 24

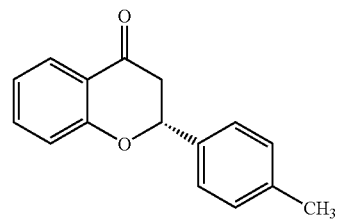

(R)-2-p-tolylchroman-4-one (10): Prepared according to general procedure using (E)-tert-butyl 2-(2-hydroxyphenylcarbonyl)-3-p-tolylprop-2-enoate (54 mg, 0.16 mmol), thiourea catalyst III (11 mg, 0.016 mmol) in 1.6 mL toluene for 36 h at −25° C. and p-toluenesulfonic acid (15 mg, 0.08 mmol) for 25 h. Purification via column chromatography with 10% EtOAc/hexanes afforded 32 mg (83%) of 10 as a white solid in 90% ee. Analytical data match those reported in the literature.[6]

Example 25

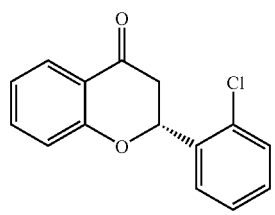

(R)-2-(2-chlorophenyl)chroman-4-one (11): Prepared according to general procedure using (E)-tert-butyl 3-(2-chlorophenyl)-2-(2-hydroxyphenylcarbonyl)prop-2-enoate (36 mg, 0.10 mmol), thiourea catalyst III (7 mg, 0.010 mmol) in 1.0 mL toluene for 36 h at −25° C. and p-toluenesulfonic acid (10 mg, 0.05 mmol) for 50 h. Purification via column chromatography with 10% EtOAc/hexanes afforded 19 mg (67%) of 11 as a white solid in 88% ee. Analytical data match those reported in the literature.[6]

Example 26

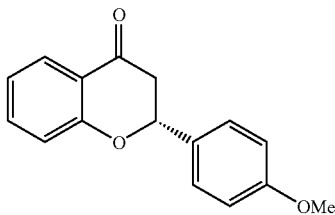

(R)-2-(4-methoxyphenyl)chroman-4-one: Prepared according to general procedure using (E)-tert-butyl 2-(2-hydroxyphenylcarbonyl)-3-(4-methoxyphenyl)prop-2-enoate (35.0 mg, 0.10 mmol), thiourea catalyst III (7 mg, 0.01 mmol) in 1.0 mL toluene for 3 d at −25° C. After completion of reaction, 100 mL sample was withdrawn to determine ee of 3-tert-butylcarboxy-(4-methoxyphenyl)chromanone 12 (90% ee). Anhydrous $MgBr_2.OEt_2$ (170 mg) was added to the remaining solution and stirred at RT for 48 h. Purification via column chromatography with 10% EtOAc/hexanes afforded 11 mg (49%) as a yellow solid in 78% ee. Analytical data match those reported in the literature.[6]

Example 27

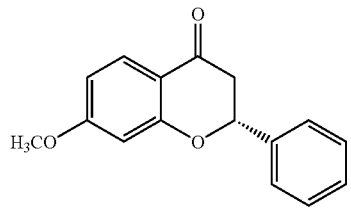

(R)-7-methoxy-2-phenylchroman-4-one (13): Prepared according to general procedure using (E)-tert-butyl 2-(2-hydroxy-4-methoxyphenylcarbonyl)-3-phenylprop-2-enoate (71 mg, 0.20 mmol), thiourea catalyst III (14 mg, 0.020 mmol) in 2.0 mL toluene for 42 h at −25° C. and p-toluenesulfonic acid (19 mg, 0.10 mmol) for 18 h. Purification via column chromatography with 10% EtOAc/hexanes afforded 36 mg (71%) of 13 as a white solid in 89% ee. $[\alpha]_D$: +58.5 (EtOH, c=0.5). Analytical data for 13: IR (film) 1683.3, 1608.6, 1442.7, 1258.9 cm$^{-1}$; $^1$H NMR (500 MHz, CDCl$_3$) δ 7.89 (d, J=8.5 Hz, 1H), 7.50-7.39 (m, 5H), 6.63 (dd, J=8.8, 2.1 Hz, 1H), 6.52 (d, J=1.5 Hz, 1H), 5.48 (dd, J=13.4, 2.4 Hz, 1H), 3.85 (s, 3H), 3.06 (dd, J=16.8, 13.4 Hz, 1H), 2.85 (dd, J=16.8, 2.8 Hz, 1H); $^{13}$C NMR (125 MHz, CDCl$_3$) δ 190.8, 166.4, 163.7, 139.0, 129.1, 129.0 (x2), 126.4, 115.4, 110.5, 101.1, 80.2, 55.9, 44.5; LRMS (electrospray): Exact mass calcd for $C_{16}H_{14}O_3$ [M]$^+$, 254.09. Found [M+1], 255.6.

Example 28

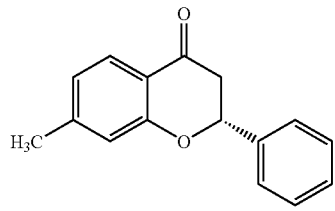

(R)-7-methyl-2-phenylchroman-4-one (14): Prepared according to general procedure using (E)-tert-butyl 2-(2-hydroxy-4-methylphenylcarbonyl)-3-phenylprop-2-enoate (51 mg, 0.15 mmol), thiourea catalyst III (10 mg, 0.020 mmol) in 1.5 mL toluene for 6 d at −25° C. and p-toluenesulfonic acid (15 mg, 0.08 mmol) for 9 h. Purification via column chromatography with 10% EtOAc/hexanes afforded 35 mg (97%) of 14 as a white solid in 90% ee. $[\alpha]_D$: +54.8 (EtOH, c=0.52). Analytical data for 14: IR (film) 1688.6, 1616.6, 1295.2, 1242.3 cm$^{-1}$; $^1$H NMR (500 MHz, CDCl$_3$) δ 7.83 (d, J=8.4 Hz, 1H), 7.49-7.38 (m, 5H), 6.89-6.87 (m, 2H), 5.46 (dd, J=13.3, 2.7 Hz, 1H), 3.06 (dd, J=16.9, 13.3 Hz, 1H), 2.87 (dd, J=16.9, 2.7 Hz, 1H) 2.34 (s, 3H); $^{13}$C NMR (125 MHz, CDCl$_3$) δ 192.0, 161.8, 148.0, 139.1, 129.1, 129.0, 127.2, 126.4, 123.2, 118.9, 118.4, 79.8, 44.9, 22.2; LRMS (electrospray): Exact mass calcd for $C_{16}H_{14}O_2$ [M]$^+$, 238.10. Found [M+1], 239.1.

Example 29

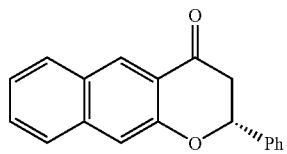

(R)-6,7-benzo-2-phenylchroman-4-one (15): Prepared according to general procedure using (E)-tert-butyl 2-(3-hydroxynaphthalene-2-carbonyl)-3-phenylprop-2-enoate (59 mg, 0.20 mmol), thiourea catalyst III (10 mg, 0.016 mmol) in 1.5 mL toluene for 8 d at −25° C. and p-toluenesulfonic acid (15 mg, 0.015 mmol) for 10 h. Purification via column chromatography with 10% EtOAc/hexanes afforded 34 mg (78%) of 15 as a yellow solid in 89% ee. $[\alpha]_D$: +31.9 (EtOH, c=0.5). Analytical data for 15: IR (film) 1722.1, 1639.5, 1255.2, 1154.6 cm$^{-1}$; $^1$H NMR (500 MHz, CDCl$_3$) δ 8.52 (s, 1H); 7.88 (d, J=8.0 Hz, 1H); 7.69 (d, J=8.5 Hz, 1H); 7.52-7.34 (m, 8H), 5.51 (d, J=12.2 Hz, 1H), 3.19 (dd, J=17.1, 12.8 Hz, 1H), 3.01 (dd, J=17.0, 3.0 Hz, 1H); $^{13}$C NMR (125 MHz, CDCl$_3$) δ 192.9, 156.9, 139.2, 138.2, 130.3, 129.5, 129.4, 129.1, 129.0, 128.8, 127.0, 126.4, 125.1, 121.8, 113.3, 79.4, 45.8; LRMS (electrospray): Exact mass calcd for $C_{19}H_{14}O_2$ [M]$^+$, 274.10. Found [M+1], 275.2.

Example 30

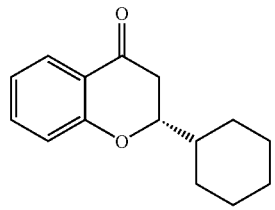

(R)-2-(cyclohexyl)chroman-4-one (16): Prepared according to general procedure using (E)-tert-butyl 3-cyclohexyl-2-(2-hydroxyphenylcarbonyl)prop-2-enoate (66 mg, 0.20 mmol), thiourea catalyst III (14 mg, 0.020 mmol) in 2.0 mL toluene for 5 d at −25° C. and p-toluenesulfonic acid (19 mg, 0.10 mmol) for 4 h. Purification via column chromatography with 10% EtOAc/hexanes afforded 30.0 mg (65%) of 16 as a white solid in 80% ee. $[\alpha]_D$: −53.0 (EtOH, c=0.5). Analytical data for 16: IR (film) 2928.8, 1689.6, 1608.8, 1467.1, 1310.1, 1229.6 cm$^{-1}$; $^1$H NMR (500 MHz, CDCl$_3$) δ 7.87 (d, J=7.3

Hz, 1H), 7.47 (t, J=7.1 Hz, 1H), 7.01-6.97 (m, 2H), 4.23-4.19 (m, 1H), 2.77-2.65 (m, 2H), 2.01-1.99 (m, 1H), 1.84-1.72 (m, 5H), 1.35-1.11 (m, 5H); $^{13}$C NMR (125 MHz, CDCl$_3$) δ 193.4, 162.1, 136.1, 127.1, 121.2 (x2), 118.1, 82.2, 42.0, 40.4, 28.5, 28.4, 26.5, 26.15, 26.09; LRMS (electrospray): Exact mass calcd for C$_{15}$H$_{18}$O$_2$ [M]$^+$, 230.13. Found [M+1], 231.7.

Example 31

One-Pot Knoevenagel/Cyclization: To a 25 mL RBF was added tert-Butyl 3-(2-hydroxyphenyl)-3-oxopropanoate 18 (71 mg, 0.3 mmol), thiourea catalyst I, (36 mg, 20 mol %), and 4 Å MS (0.50 g). The flask was purged with N$_2$. Toluene (9.0 mL), hydrocinnamaldehyde (40 μL, 0.3 mmol) and piperidinium acetate (0.025 M in toluene, 0.6 mL) were added and the heterogenous mixture was stirred at 22° C. for 2 d. The reaction was taken up in EtOAc (40 mL) and washed with brine (25 mL). The organic layer was dried with Na$_2$SO$_4$, filtered concentrated to give 93 mg of a pink oil (88%) which was decarboxylated with 6.0 mL toluene, 15 mg p-TsOH, heating to 80° C. for 9 h. The reaction was taken up in EtOAc (30 mL) and washed with brine (15 mL). The organic layer was dried with Na$_2$SO$_4$, filtered, concentrated. Purification via column chromatography with 10% EtOAc/hexanes afforded 57 mg 20 as a yellow solid (88%) in 80% ee. [α]$_D$: −59.0 (EtOH, c=0.62).

Example 32

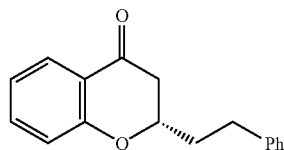

(S)-2-Phenethylchroman-4-one ((S)-Flindersiachromanone) (20). Analytical data match those reported in the literature. Kawasaki, M.; Yoshikai, H.; Kakuda, H.; Toyooka, N.; Tanaka, A.; Goto, M.; Kometani, T. *Heterocycles* 2006, 68, 483-493. Previously unreported $^{13}$C NMR (125 MHz, CDCl$_3$) δ 192.5, 161.8, 141.2, 136.3, 128.8, 128.7, 127.2, 126.4, 121.6, 121.3, 118.2, 77.0, 43.3, 36.8, 31.4.

Example 33

General Procedure for Racemic Cyclizations for HPLC Traces: To a 10 mL round bottom flask containing a magnetic stirring bar was added alkylidene compound 0.1 mmol, 30 mol % 1,8-diazabicyclo[5.4.0]undec-7-ene and 2 mL acetonitrile. The solution is stirred at 23° C. for 3-12 h. Reaction progress was monitored by TLC. After complete cyclization, 50 mol % p-toluenesulfonic acid was added to the flask and the solution was heated to 80° C., and the reaction was monitored by TLC. Upon completion of the reaction, the solution was allowed to cool and the solution was diluted with EtOAc (20 mL), poured into a separatory funnel and washed with brine. The organic layer was dried over anhydrous Na$_2$SO$_4$, filtered and concentrated to provide the crude flavanone. The crude mixture was purified via silica gel chromatography (10% EtOAc/hexanes) and concentrated in vacuo.

Example 34

As discussed above, the natural and non-natural absyssinone compounds were prepared in accordance with the preceding Knoevenagel, cyclization and decarboxylation procedures, from the corresponding β-ketoester and aldehyde compounds, as would be understood by those skilled in the art made aware of this invention.

We claim:
1. A method of using a chiral thiourea catalyst for enantioselective synthesis of a chromanone compound, said method comprising:
providing an alkylidene compound of a formula

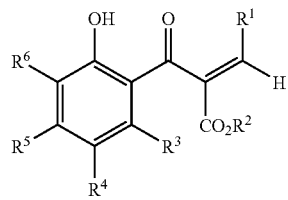

wherein R$^1$ is selected from substituted or unsubstituted alkyl, cycloalkyl, cycloalkylalkyl, alkenyl, cycloalkylalkenyl, aryl, and aralkyl moieties; R$^2$ is selected from substituted or unsubstituted branched chain about C$_3$ to about C$_6$ alkyl and about C$_3$ to about C$_9$ cycloalkyl moieties; R$^3$, R$^4$, R$^5$, and R$^6$ are independently selected from H, OR$^7$, substituted a unsubstituted alkyl and cycloalkyl moieties, and moieties where one of R$^6$ and R$^5$ together, R$^5$ and R$^4$ together, or R$^4$ and R$^3$ together form a substituted or unsubstituted C$_3$ to about C$_5$ alkylene or alkenylene moieties; and R$^7$ is selected from H and substituted or unsubstituted alkyl moieties; and
contacting said compound with a chiral thiourea catalyst compound in an amount at least partially sufficient for intramolecular conjugate addition of said alkylidene compound, to provide a chromanone compound of a formula

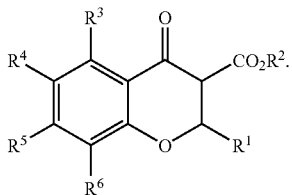

2. The method of claim 1 comprising decarboxylation of said chromanone compound.
3. The method of claim 2 wherein R$^1$ is aryl and R$^5$ is selected from H, alkyl, substituted alkyl, cycloalkyl and substituted cycloalkyl moieties.
4. The method of claim 3 wherein said catalyst is selected from compounds I, II and III.
5. The method of claim 4 wherein a said decarboxylated chromanone compound has an (R) stereochemical configuration at the C2 position thereof.
6. The method of claim 3 wherein said conjugate addition and said decarboxylation are without reaction vessel transfer.
7. The method of claim 6 wherein said catalyst is compound III.

8. The method of claim 2 wherein $R^1$ is selected from

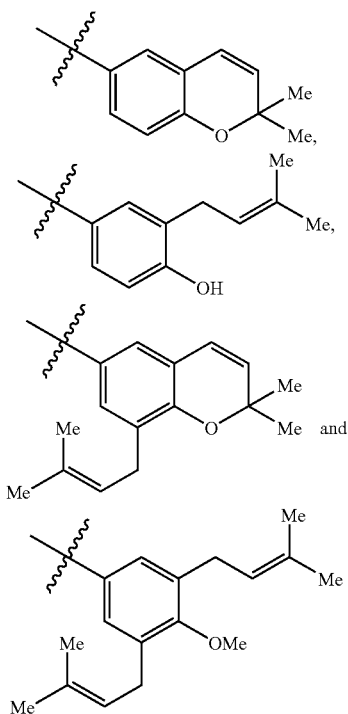

moieties, and $R^5$ is an allyl-protected hydroxy moiety.

9. The method of claim 8 wherein said catalyst is selected from compounds IV and V.

10. The method of claim 9 comprising said decarboxylation and hydroxy deprotection without reaction vessel transfer.

11. The method of claim 9 wherein said catalyst is compound IV.

12. The method of claim 11 wherein a said decarboxylated chromanone compound has an (R) stereochemical configuration at the C2 position thereof.

13. The method of claim 10 wherein said catalyst is compound V.

14. The method of claim 13 wherein a said decarboxylated chromanone compound has an (S) stereochemical configuration at the C2 position thereof.

15. A method of preparing a C2-(R)-chromanone compound, said method comprising:
providing a reaction medium comprising a mixture of a β-ketoester of a formula

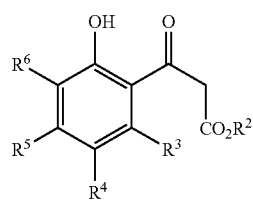

wherein $R^2$ is selected from substituted or unsubstituted branched chain about $C_3$ to about $C_6$ alkyl and about $C_3$ to about $C_9$ cycloalkyl moieties; $R^3$, $R^4$, $R^5$, and $R^6$ are independently selected from H, $OR^7$, substituted a unsubstituted alkyl and cycloalkyl moieties, and moieties where one of $R^6$ and $R^5$ together, $R^5$ and $R^4$ together, or $R^4$ and $R^3$ together form a substituted or unsubstituted $C_3$ to about $C_5$ alkylene or alkenylene moieties; and $R^7$ is selected from H and substituted or unsubstituted alkyl moieties; an aldehyde of a formula $R^1CHO$, where $R^1$ is selected from substituted and unsubstituted alkyl, cycloalkyl, cycloalkylalkyl, alkenyl, cycloalkylalkenyl, aryl and aralkyl moieties; an organoamine base; and a thiourea catalyst compound, said catalyst selected from compounds I, II and III, to provide a C3-carboxy substituted chromanone compound; and
contacting said reaction medium with a $C_1$ to about $C_{10}$ organic acid, to decarboxylate said chromanone compound, said preparation without reaction vessel transfer.

16. The method of claim 15 wherein said thiourea catalyst is compound I.

17. The method of claim 15 wherein $R^1$ is a phenyl-substituted ethyl moiety.

* * * * *